(12) United States Patent
Cruse

(10) Patent No.: US 7,301,042 B2
(45) Date of Patent: *Nov. 27, 2007

(54) BLOCKED MERCAPTOSILANE HYDROLYZATES AS COUPLING AGENTS FOR MINERAL-FILLED ELASTOMER COMPOSITIONS

(76) Inventor: Richard W. Cruse, 171 Montross Rd., Yorktown Heights, NY (US) 10598

( * ) Notice: Subject to any disclaimer, the term of this patent is extended or adjusted under 35 U.S.C. 154(b) by 0 days.

This patent is subject to a terminal disclaimer.

(21) Appl. No.: 10/128,804

(22) Filed: Apr. 23, 2002

(65) Prior Publication Data

US 2003/0199619 A1   Oct. 23, 2003

(51) Int. Cl.
   *C07F 7/08*   (2006.01)
(52) U.S. Cl. ...................................... 556/429
(58) Field of Classification Search ............... 524/261; 556/400

See application file for complete search history.

(56) References Cited

U.S. PATENT DOCUMENTS

| | | | |
|---|---|---|---|
| 3,692,812 A | 9/1972 | Berger ..................... 260/448.2 |
| 3,922,436 A | 11/1975 | Bell et al. .................. 428/375 |
| 3,957,718 A | 5/1976 | Pochert et al. ................ 260/38 |
| 4,184,998 A | 1/1980 | Shippy et al. ............ 260/42.15 |
| 4,519,430 A | 5/1985 | Ahmad et al. ............... 152/209 |
| 5,116,886 A | 5/1992 | Wolff et al. ................. 523/209 |
| 6,127,468 A | 10/2000 | Cruse et al. ................ 524/225 |
| 6,204,339 B1 | 3/2001 | Waldman et al. |
| 6,608,125 B2 * | 8/2003 | Cruse et al. ................ 524/262 |
| 6,683,135 B2 * | 1/2004 | Cruse et al. ................ 525/100 |
| 7,074,876 B2 * | 7/2006 | Cruse et al. .................. 528/44 |
| 7,078,551 B2 * | 7/2006 | Cruse et al. .................. 558/44 |
| 7,138,537 B2 * | 11/2006 | Cruse et al. ................ 556/457 |

FOREIGN PATENT DOCUMENTS

| | | |
|---|---|---|
| AU | 10082-97 | 7/1997 |
| AU | 730753 | 3/2001 |
| EP | 0631982 A2 | 1/1995 |
| JP | 63-270751 | 11/1988 |
| WO | WO-99/09036 | * 2/1999 |

OTHER PUBLICATIONS

U.S. Appl. No. 09/986,515, filed Nov. 2001, Cruse et al.

* cited by examiner

*Primary Examiner*—Samuel Barts
(74) *Attorney, Agent, or Firm*—Dominick G. Vicari

(57) ABSTRACT

Rubber composition intended for the manufacture of tire casings which have improved hysteretic properties and scorch safety, based on at least one elastomer and silica by way of reinforcing filler enclosing a reinforcing additive consisting of the mixture and/or the product of in situ reaction of at least one functionalized polyorganosiloxane compound containing, per molecule, at least one functional siloxy unit capable of bonding chemically and/or physically to the surface hydroxyl sites of the silica particles and at least one functionalized organosilane compound containing, per molecule, at least one functional group capable of bonding chemically and/or physically to the polyorganosiloxane and/or the hydroxyl sites of the silica particles and at least one other functional group capable of bonding chemically and/or physically to the polymer chains.

18 Claims, 4 Drawing Sheets

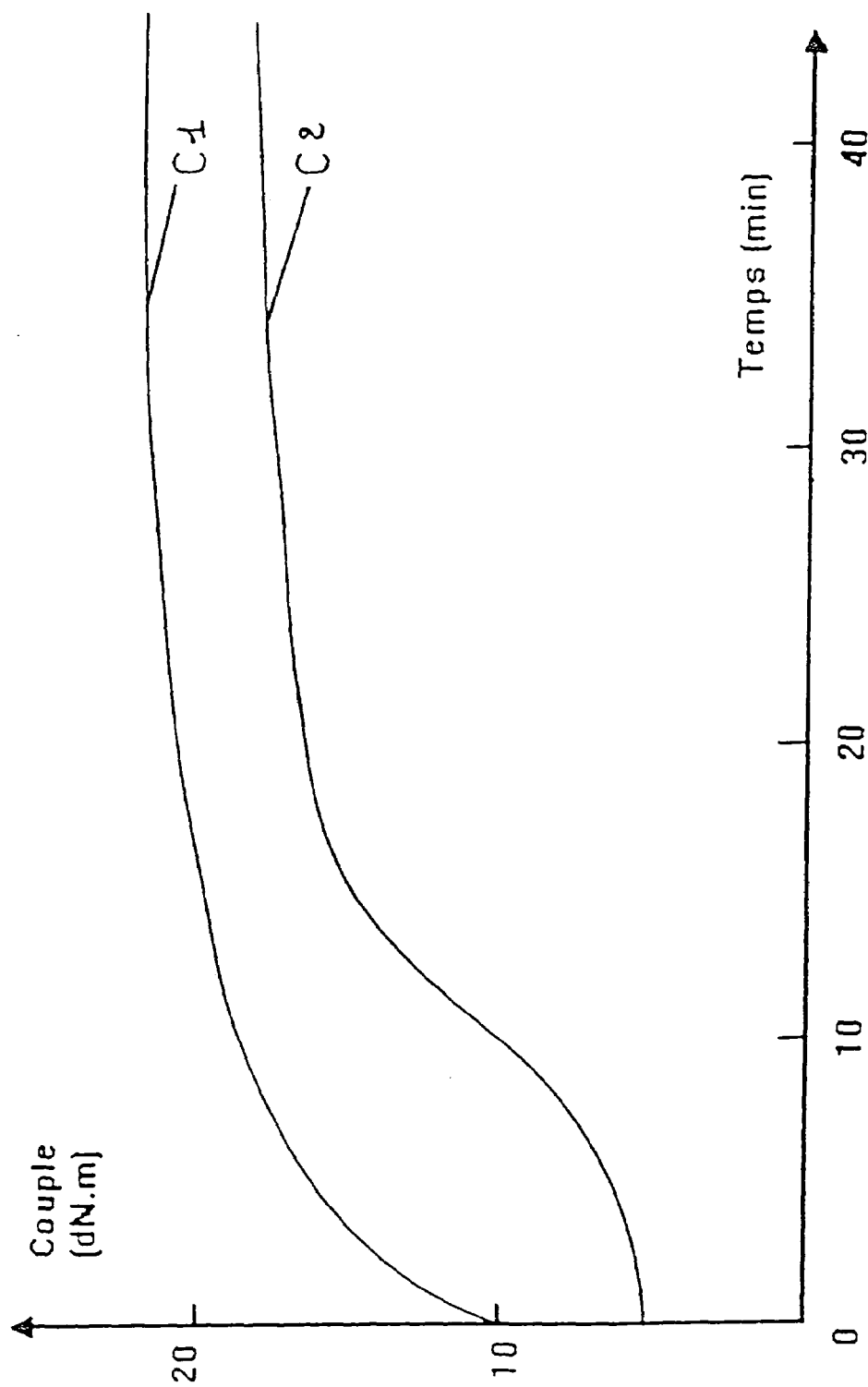
FIGURE N°1

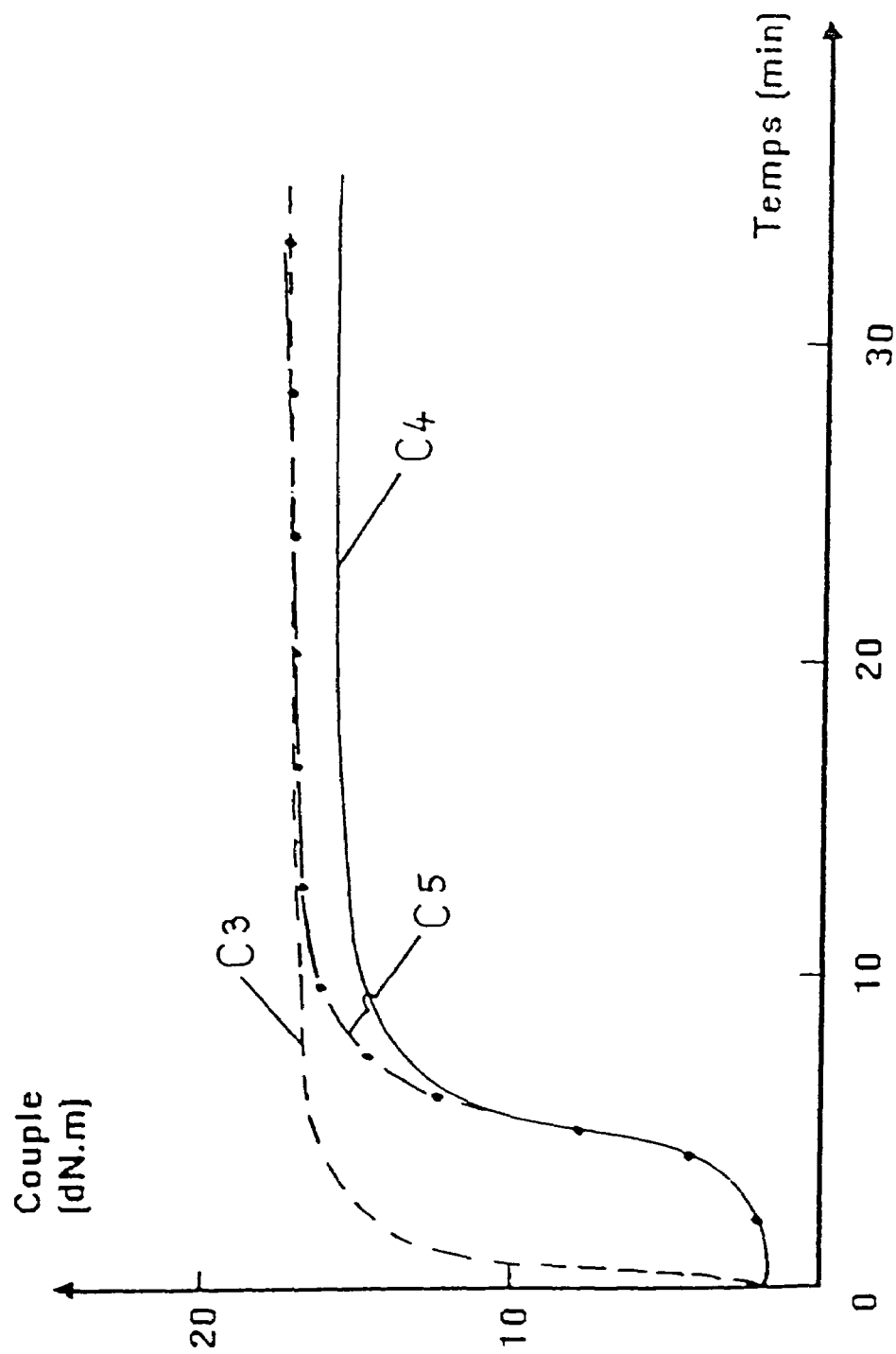

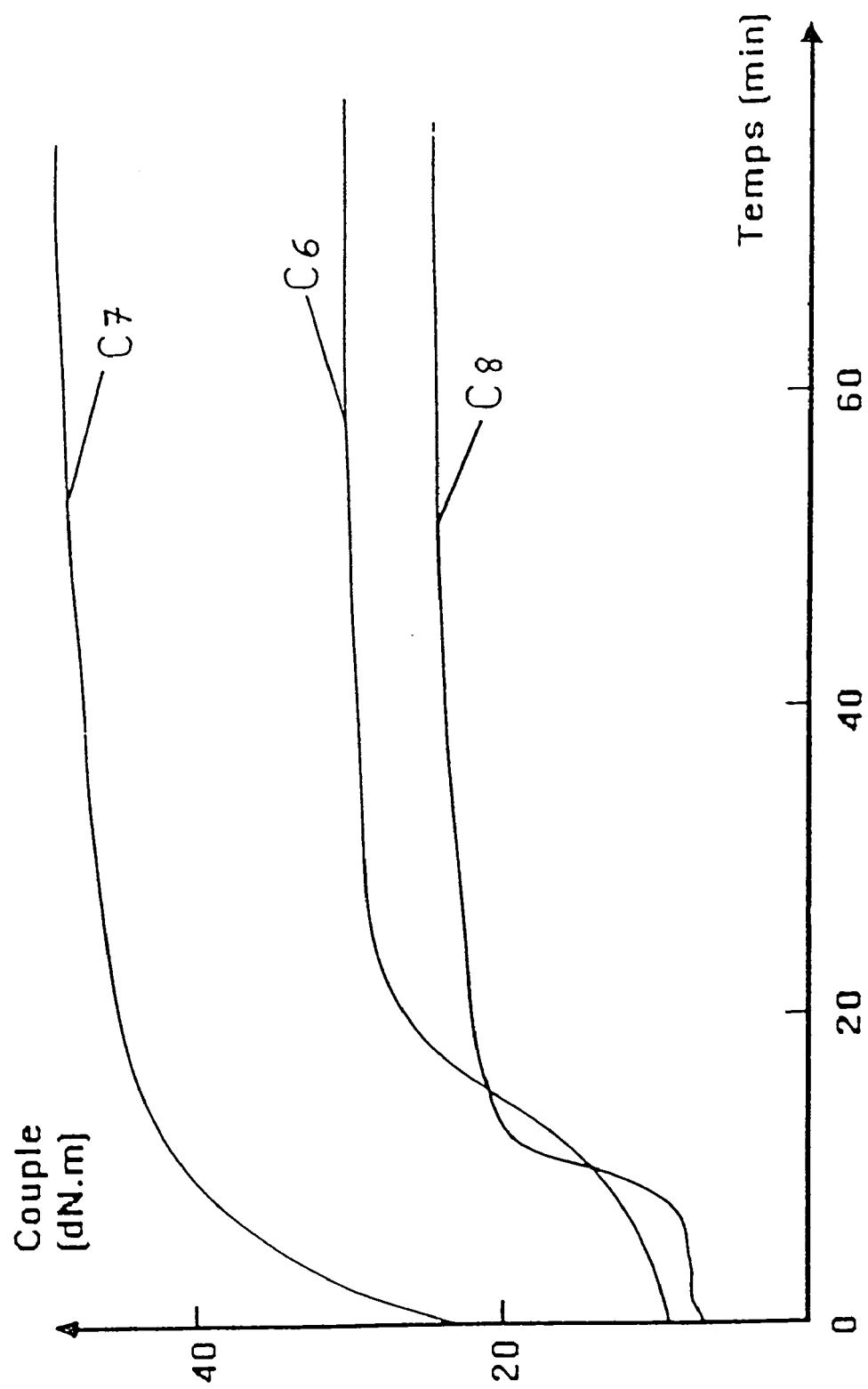

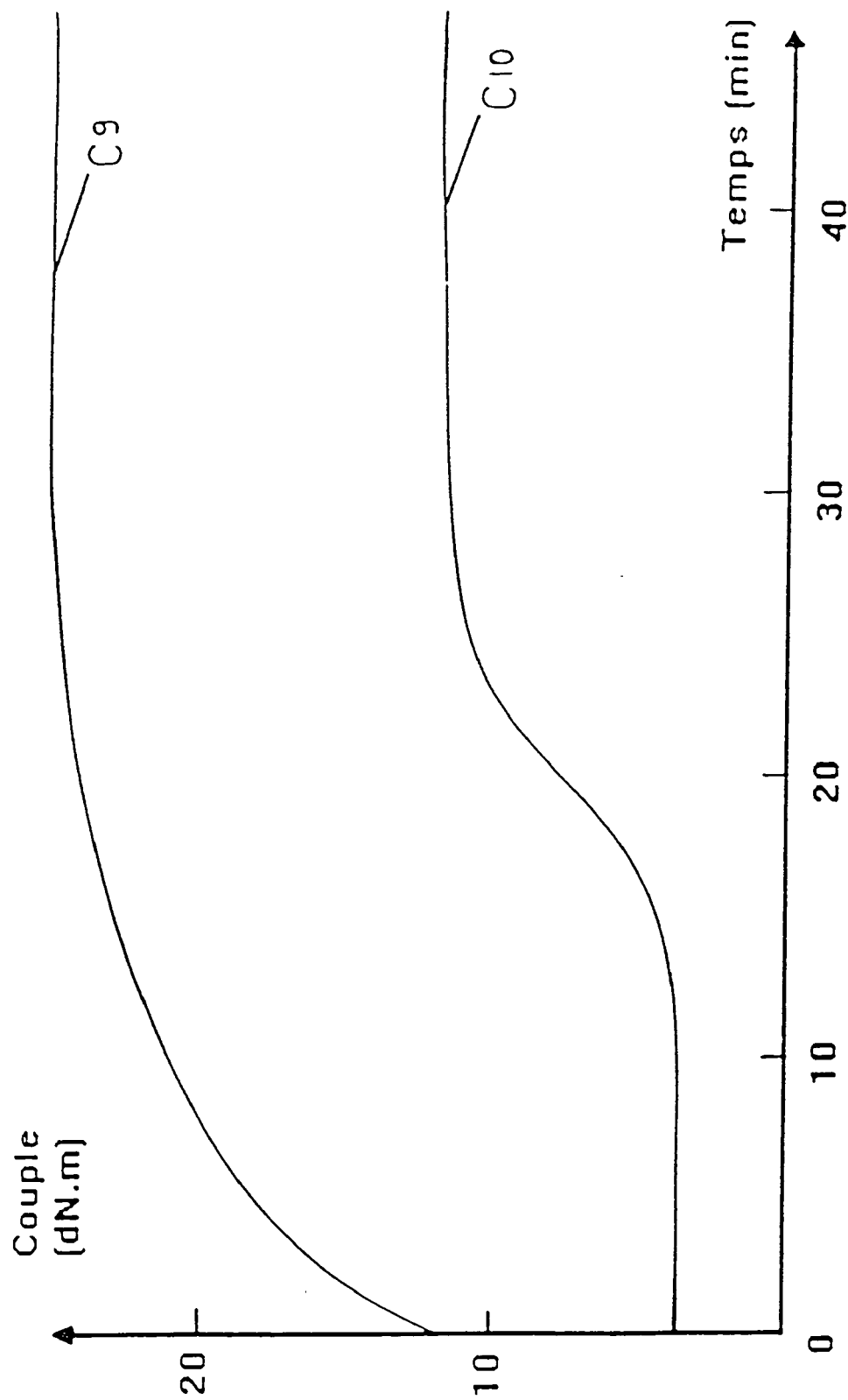
FIGURE N°4

BLOCKED MERCAPTOSILANE HYDROLYZATES AS COUPLING AGENTS FOR MINERAL-FILLED ELASTOMER COMPOSITIONS

BACKGROUND OF THE INVENTION

1. Field of the Invention

The present invention relates to the composition, preparation, and use in elastomer compositions of latent mercaptosilane coupling agents containing siloxane bonds. These coupling agents represent an improvement over the prior art in that their use is accompanied by reduced volatile organic compound (VOC) emissions.

2. Description of Related Art

Latent mercaptosilane coupling agents known in the art contain hydrolyzable groups that are converted to volatile byproducts when the coupling agents react with the fillers used in the rubber compositions.

The majority of art in the use of sulfur-containing coupling agents in rubber involves silanes containing one or more of the following chemical bond types: S—H (mercapto), S—S (disulfide or polysulfide), or C=S (thiocarbonyl). Mercaptosilanes have offered superior coupling at substantially reduced loadings; however, their high chemical reactivity with organic polymers leads to unacceptably high viscosities during processing and premature curing (scorch). Their undesirability is aggravated by their odor. As a result, other, less reactive coupling agents have been found. Hence, a compromise must be found between coupling and the associated final properties, processability, and required loading levels, which invariably leads to the need to use substantially higher coupling agent loadings than would be required with mercaptosilanes, and often also to the need to deal with less than optimal processing conditions, both of which lead to higher costs.

Acylthioalkyl silanes, such as $CH_3C(=O)S(CH_2)_{1-3}Si(OR)_3$ and $HOC(=O)CH_2CH_2C(=O)S(CH_2)_3Si(OC_2H_5)_3$ are disclosed in Voronkov, M. G. et al. in *Inst. Org. Khim.*, Irkutsk, Russia and U.S. Pat. No. 3,922,436, respectively.

U.S. Pat. No. 3,957,718 discloses compositions containing silica, phenoplasts or aminoplasts, and silanes, such as xanthates, thioxanthates, and dithiocarbamates; however, it does not disclose or suggest the use of these silanes as latent mercaptosilane coupling agents, nor does it suggest or disclose the advantage of using them as a source of latent mercaptosilane.

U.S. Pat. Nos. 4,184,998 and 4,519,430 disclose the blocking of a mercaptosilane with an isocyanate to form a solid that is added to a tire composition, which mercaptan reacts into the tire during heating, which could happen at any time during processing since this is a thermal mechanism. The purpose of this silane is to avoid the sulfur smell of the mercaptosilane, not to improve the processing of the tire. Moreover, the isocyanate used has toxicity issues when used to make the silane and when released during rubber processing.

Australian Patent AU-A-10082/97 discloses the use in rubber of silanes of the structure represented by

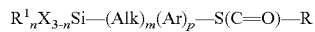

where $R^1$ is phenyl or alkyl; X is halogen, alkoxy, cycloalkoxy, acyloxy, or OH; Alk is alkyl; Ar is aryl; R is alkyl, alkenyl, or aryl; n is 0 to 2; and m and p are each 0 or 1, but not both zero. This patent, however, stipulates that compositions of the structures of the above formula must be used in conjunction with functionalized siloxanes. In addition, the patent does not disclose or suggest the use of compounds of Formula (1P) as latent mercaptosilane coupling agents, nor does it disclose or suggest the use of these compounds in any way which would give rise to the advantages of using them as a source of latent mercaptosilane.

JP 63270751 A2 discloses the use of compounds represented by the general formula $CH_2=C(CH_3)C(=O)S(CH_2)_{1-6}Si(OCH_3)_3$ in tire tread compositions; but these compounds are not desirable because the unsaturation α,β to the carbonyl group of the thioester has the undesirable potential to polymerize during the compounding process or during storage.

There remains a need for effective latent coupling agents which exhibit the advantages of mercaptosilanes without exhibiting the disadvantages such as described herein.

SUMMARY OF THE INVENTION

The conversion of a portion of the hydrolyzable groups of the latent mercaptosilanes into siloxane bonds liberates a portion of the volatile by-products prior to the use of the coupling agents in the elastomer, via their conversion to the corresponding mercaptosiloxane coupling agents of the invention described herein. The latent mercaptosiloxane coupling agents retain the function of the latent mercaptosilanes, but with the accompaniment of lower VOC emissions and with a reduced loading level requirement.

Thioester-functional alkoxysiloxanes are introduced into the elastomer composition as the source of the coupling agents. The latent thioester group serves a dual function during the mixing process. First, it keeps the coupling agent inactive during the mixing process so as to prevent premature cure and second, it serves as a hydrophobating agent for the filler so as to enhance filler dispersion in the polymer matrix. It also serves to minimize filler re-agglomeration after the mixing process (Payne Effect). Following the mixing process, the latent thioester group is removed by a suitable deblocking agent added with the curatives. This generates the active mercapto derivative, which then chemically binds to the polymer during the curing process, thereby completing the coupling of polymer to filler.

The present invention is directed to the use of siloxane derivatives of latent mercaptosilane coupling agents, whereby VOC emissions during the elastomer compounding process are reduced. The invention also presents a way of reducing the quantity of coupling agent required for the elastomer composition.

More particularly, the present invention is directed to a blocked mercaptosilane condensate comprising at least one component whose chemical structure is represented by Formula 1:

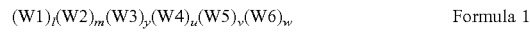   Formula 1 wherein:

m, y, u, v, and w are independently any integer from zero to 10,000;

l is any integer from 1 to 10,000;

W1 is a hydrolyzable blocked mercaptosilane fragment derived from a hydrolyzable blocked mercaptosilane by replacement of at least one hydrolyzable group with one end of a siloxane oxygen (—O—) group that is represented by either Formula 2 or Formula 3:

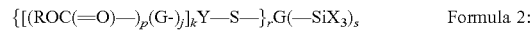   Formula 2:

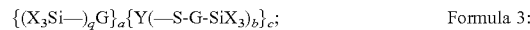   Formula 3:

W2 is a hydrolyzable mercaptosilane fragment derived from a hydrolyzable mercaptosilane by replacement of at least one hydrolyzable group with one end of a siloxane oxygen (—O—) group that is represented by Formula 4:

$$\{[(ROC(=O)—)_p(G-)_j]_k Y—S—\}_{r-d} G(—SH)_d(—SiX_3)_s;\quad \text{Formula 4:}$$

W3 is a hydrolyzable polysulfide silane fragment derived from a polysulfide silane by replacement of at least one hydrolyzable group with one end of a siloxane oxygen (—O—) group that is represented by Formula 5:

$$X^1X^2X^3Si-G^1-S_x-G^1-SiX^1X^2X^3;\quad \text{Formula 5:}$$

W4 is a hydrolyzable alkyl silane fragment derived from a hydrolyzable alkyl silane by replacement of at least one hydrolyzable group with one end of a siloxane oxygen (—O—) group that can be represented by Formula 6:

$$Y^1Y^2Y^3Si—R^2;\quad \text{Formula 6:}$$

W5 is a hydrolyzable bis silyl alkane fragment derived from a hydrolyzable bis silyl alkane by replacement of at least one hydrolyzable group with one end of a siloxane oxygen (—O—) group that is represented by Formula 7:

$$Z^1Z^2Z^3Si-J-SiZ^1Z^2Z^3;\quad \text{Formula 7:}$$

W6 is a hydrolyzable tris silyl alkane fragment derived from a hydrolyzable tris silyl alkane by replacement of at least one hydrolyzable group with one end of a siloxane oxygen (—O—) group that is represented by either Formula 8 or Formula 9:

$$(Z^1Z^2Z^3Si—CH_2CH_2—)_3C_6H_9 \quad \text{Formula 8}$$

$$(Z^1Z^2Z^3Si—CH_2CH_2CH_2—)_3N_3C_3O_3;\quad \text{Formula 9}$$

wherein, in the preceding Formulae 2 through 9:

Y is a polyvalent species $(Q)_zA(=E)$;

A is selected from the group consisting of carbon, sulfur, phosphorus, and sulfonyl;

E is selected from the group consisting of oxygen, sulfur, and NR;

each G is independently selected from the group consisting of monovalent and polyvalent moieties derived by substitution of alkyl, alkenyl, aryl, or aralkyl moieties, wherein G comprises from 1 to 18 carbon atoms; provided that G is not such that the silane would contain an α,β-unsaturated carbonyl including a carbon-carbon double bond next to the thiocarbonyl group, and provided that, if G is univalent, i.e., if p is 0, G can be hydrogen;

in each case, the atom A attached to the unsaturated heteroatom E is attached to the sulfur, which in turn is linked via a group G to the silicon atom;

Q is selected from the group consisting of oxygen, sulfur, and (—NR—);

each R is independently selected from the group consisting of hydrogen; straight, cyclic, or branched alkyl that may or may not contain unsaturation; alkenyl groups; aryl groups; and aralkyl groups, wherein each R, other than where R is hydrogen, comprises from 1 to 18 carbon atoms;

each X is independently selected from the group consisting of —Cl, —Br, RO—, RC(=O)O—, $R_2C=NO—$, $R_2NO—$, $R_2N—$, —R, —$(OSiR_2)_t(OSiR_3)$, and (—O—)$_{0.5}$ wherein each R is as above and at least one X is not —R;

$R^1$, $R^2$, and $R^3$ are independently selected from the group consisting of hydrocarbon fragments obtained by removal of one hydrogen atom from a hydrocarbon having from 1 to 20 carbon atoms including aryl groups and any branched or straight chain alkyl, alkenyl, arenyl, or aralkyl groups;

each J, and $G^1$ are independently selected from the group consisting of hydrocarbon fragments obtained by removal of two hydrogen atom from a hydrocarbon having from 1 to 20 carbon atoms including arylene groups and any branched or straight chain alkylene, alkenylene, arenylene, or aralkylene groups;

each $X^1$ is a hydrolyzable moiety independently selected from the group consisting of —Cl, —Br, —OH, —$OR^1$, $R^1C(=O)O—$, —O—N=$CR^1_2$, and (—O—)$_{0.5}$;

each $X^2$ and $X^3$ is independently selected from the group consisting of hydrogen, the members listed above for $R^1$, and the members listed above for $X^1$;

at least one occurrence of $X^1$, $X^2$, and $X^3$ is (—O—)$_{0.5}$;

$Y^1$ is a moiety selected from hydrolyzable groups consisting of —Cl, —Br, —OH, —OR, $R^2C(=O)O—$, —O—N=$CR^2_2$, and (—O—)$_{0.5}$;

$Y^2$ and $Y^3$ are independently selected from the group consisting of hydrogen, the members listed above for $R^2$, and the members listed above for $Y^1$; and at least one occurrence of $Y^1$, $Y^2$, and $Y^3$ is (—O—)$_{0.5}$.

$Z^1$ is selected from the hydrolyzable groups consisting of —Cl, —Br, —OH, —$OR^3$, $R^3C(=O)O—$, —O—N=$CR^3_2$, and (—O—)$_{0.5}$;

$Z^2$ and $Z^3$ are independently selected from the group consisting of hydrogen, the members listed above for $R^3$, and the members listed above for $Z^1$;

at least one occurrence of $Z^1$, $Z^2$, and $Z^3$ in Formula 7 is (—O—)$_{0.5}$;

$C_6H_9$ in Formula 8 represents any cyclohexane fragment obtainable by removal of three hydrogen atoms from a cyclohexane molecule;

$N_3C_3O_3$ in Formula 9 represents N,N',N''-trisubstituted cyanurate;

a is 0 to 7;
b is 1 to 3;
c is 1 to 6;
d is 1 to r;
j is 0 or 1, but it may be 0 if, and only if, p is 1;
k is 1 to 2;
p is 0 to 5;
q is 0 to 6;
r is 1 to 3;
s is 1 to 3;
t is 0 to 5;
x is 2 to 20;
z is 0 to 2;

provided that:
(a) if A is carbon, sulfur, or sulfonyl, then
  (i) a+b is 2, and
  (ii) k is 1;
(b) if A is phosphorus, then a+b is 3 unless both
  (i) c is greater than 1, and
  (ii) b is 1,
in which case a is c+1; and
c) if A is phosphorus, then k is 2.

In another aspect, the present invention is directed to a composition comprising at least one organic polymer, at least one inorganic filler, and at least one blocked mercaptosilane condensate comprising at least one component whose chemical structure is represented by Formula 1:

$$(W1)_l(W2)_m(W3)_y(W4)_u(W5)_v(W6)_w \quad \text{Formula 1}$$

wherein:

m, y, u, v, and w are independently any integer from zero to 10,000;

l is any integer from 1 to 10,000;

W1 is a hydrolyzable blocked mercaptosilane fragment derived from a hydrolyzable blocked mercaptosilane by replacement of at least one hydrolyzable group with one end of a siloxane oxygen (—O—) group that is represented by either Formula 2 or Formula 3:

$$\{[(ROC(=O)-)_p(G-)_j]_kY-S-\}_rG(-SiX_3)_s \quad \text{Formula 2:}$$

$$\{(X_3Si-)_qG\}_a\{Y(-S-G-SiX_3)_b\}_c; \quad \text{Formula 3:}$$

W2 is a hydrolyzable mercaptosilane fragment derived from a hydrolyzable mercaptosilane by replacement of at least one hydrolyzable group with one end of a siloxane oxygen (—O—) group that is represented by Formula 4:

$$\{[(ROC(=O)-)_p(G-)_j]_kY-S-\}_{r-d}G(-SH)_d(-SiX_3)_s; \quad \text{Formula 4:}$$

W3 is a hydrolyzable polysulfide silane fragment derived from a polysulfide silane by replacement of at least one hydrolyzable group with one end of a siloxane oxygen (—O—) group that is represented by Formula 5:

$$X^1X^2X^3Si-G^1-S_x-G^1-SiX^1X^2X^3; \quad \text{Formula 5:}$$

W4 is a hydrolyzable alkyl silane fragment derived from a hydrolyzable alkyl silane by replacement of at least one hydrolyzable group with one end of a siloxane oxygen (—O—) group that can be represented by Formula 6:

$$Y^1Y^2Y^3Si-R^2; \quad \text{Formula 6:}$$

W5 is a hydrolyzable bis silyl alkane fragment derived from a hydrolyzable bis silyl alkane by replacement of at least one hydrolyzable group with one end of a siloxane oxygen (—O—) group that is represented by Formula 7:

$$Z^1Z^2Z^3Si-J-SiZ^1Z^2Z^3; \quad \text{Formula 7:}$$

W6 is a hydrolyzable tris silyl alkane fragment derived from a hydrolyzable tris silyl alkane by replacement of at least one hydrolyzable group with one end of a siloxane oxygen (—O—) group that is represented by either Formula 8 or Formula 9:

$$(Z^1Z^2Z^3Si-CH_2CH_2-)_3C_6H_9 \quad \text{Formula 8:}$$

$$(Z^1Z^2Z^3Si-CH_2CH_2CH_2-)_3N_3C_3O_3; \quad \text{Formula 9:}$$

wherein, in the preceding Formulae 2 through 9:

Y is a polyvalent species $(Q)_zA(=E)$;

A is selected from the group consisting of carbon, sulfur, phosphorus, and sulfonyl;

E is selected from the group consisting of oxygen, sulfur, and NR;

each G is independently selected from the group consisting of monovalent and polyvalent moieties derived by substitution of alkyl, alkenyl, aryl, or aralkyl moieties, wherein G comprises from 1 to 18 carbon atoms; provided that G is not such that the silane would contain an α,β-unsaturated carbonyl including a carbon-carbon double bond next to the thiocarbonyl group, and provided that, if G is univalent, i.e., if p is 0, G can be hydrogen;

in each case, the atom A attached to the unsaturated heteroatom E is attached to the sulfur, which in turn is linked via a group G to the silicon atom;

Q is selected from the group consisting of oxygen, sulfur, and (—NR—);

each R is independently selected from the group consisting of hydrogen; straight, cyclic, or branched alkyl that may or may not contain unsaturation; alkenyl groups; aryl groups; and aralkyl groups, wherein each R, other than where R is hydrogen, comprises from 1 to 18 carbon atoms;

each X is independently selected from the group consisting of —Cl, —Br, RO—, RC(=O)O—, $R_2C=NO$—, $R_2NO$—, $R_2N$—, —R, —(OSiR$_2$)$_t$(OSiR$_3$), and (—O—)$_{0.5}$ wherein each R is as above and at least one X is not —R;

$R^1$, $R^2$, $R^3$ are independently selected from the group consisting of hydrocarbon fragments obtained by removal of one hydrogen atom from a hydrocarbon having from 1 to 20 carbon atoms including aryl groups and any branched or straight chain alkyl, alkenyl, arenyl, or aralkyl groups;

each J, and $G^1$ are independently selected from the group consisting of hydrocarbon fragments obtained by removal of two hydrogen atom from a hydrocarbon having from 1 to 20 carbon atoms including arylene groups and any branched or straight chain alkylene, alkenylene, arenylene, or aralkylene groups;

each $X^1$ is a hydrolyzable moiety independently selected from the group consisting of —Cl, —Br, —OH, —OR$^1$, $R^1C(=O)O$—, —O—N=CR$^1_2$, and (—O—)$_{0.5}$;

each $X^2$ and $X^3$ is independently selected from the group consisting of hydrogen, the members listed above for $R^1$, and the members listed above for $X^1$;

at least one occurrence of $X^1$, $X^2$, and $X^3$ is (—O—)$_{0.5}$;

$Y^1$ is a moiety selected from hydrolyzable groups consisting of —Cl, —Br, —OH, —OR, $R^2C(=O)O$—, —O—N=CR$^2_2$, and (—O—)$_{0.5}$;

$Y^2$ and $Y^3$ are independently selected from the group consisting of hydrogen, the members listed above for $R^2$, and the members listed above for $Y^1$; and at least one occurrence of $Y^1$, $Y^2$, and $Y^3$ is (—O—)$_{0.5}$.

$Z^1$ is selected from the hydrolyzable groups consisting of —Cl, —Br, —OH, —OR$^3$, $R^3C(=O)O$—, —O—N=CR$^3_2$, and (—O—)$_{0.5}$;

$Z^2$ and $Z^3$ are independently selected from the group consisting of hydrogen, the members listed above for $R^3$, and the members listed above for $Z^1$;

at least one occurrence of $Z^1$, $Z^2$, and $Z^3$ in Formula 7 is (—O—)$_{0.5}$;

$C_6H_9$ in Formula 8 represents any cyclohexane fragment obtainable by removal of three hydrogen atoms from a cyclohexane molecule;

$N_3C_3O_3$ in Formula 9 represents N,N',N"-trisubstituted cyanurate;

a is 0 to 7;
b is 1 to 3;
c is 1 to 6;
d is 1 to r;
j is 0 or 1, but it may be 0 if, and only if, p is 1;
k is 1 to 2;
p is 0 to 5;
q is 0 to 6;
r is 1 to 3;
s is 1 to 3;
t is 0 to 5;
x is 2 to 20;
z is 0 to 2;
provided that:
(a) if A is carbon, sulfur, or sulfonyl, then
  (i) a+b is 2, and
  (ii) k is 1;
(b) if A is phosphorus, then a+b is 3 unless both
  (i) c is greater than 1, and
  (ii) b is 1,
  in which case a is c+1; and
c) if A is phosphorus, then k is 2.

In still another aspect, the present invention is directed to an article of manufacture comprising the composition described in the previous paragraph.

DESCRIPTION OF THE PREFERRED EMBODIMENTS

Silane Structures

The blocked mercaptosilane condensates described herein comprise at least one component whose chemical structure can be represented by Formula 1.

$$(W1)_l(W2)_m(W3)_y(W4)_u(W5)_v(W6)_w \quad \text{Formula 1}$$

In Formula 1, m, y, u, v, and w are independently any integer from zero to 10,000; l is any integer from 1 to 10,000. Preferably, l+m+y+u+v+w is equal to at least 2.

W1, W2, W3, W4, W5, and W6 (the "W groups") represent the building blocks of the blocked mercaptosilane condensates described herein.

In Formula 1:

W1 is a hydrolyzable blocked mercaptosilane fragment derived from a hydrolyzable blocked mercaptosilane by replacement of at least one hydrolyzable group with one end of a siloxane oxygen (—O—) group that can be represented by either Formula 2 or Formula 3:

$$\{[(ROC(=O)-)_p(G-)_j]_kY-S-\}_rG(-SiX_3)_s \quad \text{Formula 2}$$

$$\{(X_3Si-)_qG\}_a\{Y(-S-G-SiX_3)_b\}_c \quad \text{Formula 3}$$

W2 is a hydrolyzable mercaptosilane fragment derived from a hydrolyzable mercaptosilane by replacement of at least one hydrolyzable group with one end of a siloxane oxygen (—O—) group that can be represented by Formula 4:

$$\{[(ROC(=O)-)_p(G-)_j]_kY-S-\}_{r-d}G(-SH)_d(-SiX_3)_s \quad \text{Formula 4}$$

W3 is a hydrolyzable polysulfide silane fragment derived from a polysulfide silane by replacement of at least one hydrolyzable group with one end of a siloxane oxygen (—O—) group that can be represented by Formula 5:

$$X^1X^2X^3Si\text{-}G^1\text{-}S_x\text{-}G^1\text{-}SiX^1X^2X^3 \quad \text{Formula 5}$$

W4 is a hydrolyzable alkyl silane fragment derived from a hydrolyzable alkyl silane by replacement of at least one hydrolyzable group with one end of a siloxane oxygen (—O—) group that can be represented by Formula 6:

$$Y^1Y^2Y^3Si-R^2 \quad \text{Formula 6}$$

W5 is a hydrolyzable bis silyl alkane fragment derived from a hydrolyzable bis silyl alkane by replacement of at least one hydrolyzable group with one end of a siloxane oxygen (—O—) group that can be represented by Formula 7:

$$Z^1Z^2Z^3Si\text{-}J\text{-}SiZ^1Z^2Z^3 \quad \text{Formula 7}$$

W6 is a hydrolyzable tris silyl alkane fragment derived from a hydrolyzable tris silyl alkane by replacement of at least one hydrolyzable group with one end of a siloxane oxygen (—O—) group that can be represented by either Formula 8 or Formula 9:

$$(Z^1Z^2Z^3Si-CH_2CH_2-)_3C_6H_9 \quad \text{Formula 8}$$

$$(Z^1Z^2Z^3Si-CH_2CH_2CH_2-)_3N_3C_3O_3 \quad \text{Formula 9}$$

In the preceding Formulae 2 through 9:

Y is a polyvalent species $(Q)_zA(=E)$, preferably selected from the group consisting of —C(=NR)—; —SC(=NR)—; —SC(=O)—; —(—NR)C(=O)—; —(—NR)C(=S)—; —OC(=O)—; —OC(=S)—; —C(=O)—; —SC(=S)—; —C(=S)—; —S(=O)—; —S(=O)$_2$—; —OS(=O)$_2$—; —(—NR)S(=O)$_2$—; —SS(=O)—; —OS(=O)—; (—NR)S(=O)—; —SS(=O)$_2$—; (—S)$_2$P(=O)—; —(—S)P(=O)—; —P(=O)(—)$_2$; (—S)$_2$P(=S)—; —(—S)P(=S)—; —P(=S)(—)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—;

A is selected from the group consisting of carbon, sulfur, phosphorus, and sulfonyl;

E is selected from the group consisting of oxygen, sulfur, and NR;

each G is independently selected from the group consisting of monovalent and polyvalent moieties derived by substitution of alkyl, alkenyl, aryl, or aralkyl moieties, wherein G comprises from 1 to 18 carbon atoms; provided that G is not such that the silane would contain an α,β-unsaturated carbonyl including a carbon-carbon double bond next to the thiocarbonyl group, and provided that, if G is univalent (i.e., if p is 0), G can be hydrogen;

in each case, the atom (A) attached to the unsaturated heteroatom (E) is attached to the sulfur, which in turn is linked via a group G to the silicon atom;

Q is selected from the group consisting of oxygen, sulfur, and (—NR—);

each R is independently selected from the group consisting of hydrogen; straight, cyclic, or branched alkyl that may or may not contain unsaturation; alkenyl groups; aryl groups; and aralkyl groups, wherein each R, other than hydrogen, comprises from 1 to 18 carbon atoms;

each X is independently selected from the group consisting of —Cl, —Br, RO—, RC(=O)O—, R$_2$C=NO—, R$_2$NO—, R$_2$N—, —R, —(OSiR$_2$)$_t$(OSiR$_3$), and (—O—)$_{0.5}$ wherein each R is as above and at least one X is not —R;

R$^1$, R$^2$, R$^3$ are independently selected from the group consisting of hydrocarbon fragments obtained by removal of one hydrogen atom from a hydrocarbon having from 1 to 20 carbon atoms including aryl groups and any branched or straight chain alkyl, alkenyl, arenyl, or aralkyl groups;

each J, and G$^1$ are independently selected from the group consisting of hydrocarbon fragments obtained by removal of two hydrogen atom from a hydrocarbon having from 1 to 20 carbon atoms including arylene groups and any branched or straight chain alkylene, alkenylene, arenylene, or aralkylene groups;

each X$^1$ is a hydrolyzable moiety independently selected from the group consisting of —Cl, —Br, —OH, —OR$^1$, R$^1$C(=O)O—, —O—N=CR$^1$$_2$, and (—O—)$_{0.5}$;

each X$^2$ and X$^3$ is independently selected from the group consisting of hydrogen, the members listed above for R$^1$, and the members listed above for X$^1$;

at least one occurrence of X$^1$, X$^2$, and X$^3$ is (—O—)$_{0.5}$;

Y$^1$ is a moiety selected from hydrolyzable groups consisting of —Cl, —Br, —OH, —OR, R$^2$C(=O)O—, —O—N=CR$^2$$_2$, and (—O—)$_{0.5}$;

Y$^2$ and Y$^3$ are independently selected from the group consisting of hydrogen, the members listed above for R$^2$, and the members listed above for Y$^1$; and at least one occurrence of Y$^1$, Y$^2$, and Y$^3$ is (—O—)$_{0.5}$.

Z$^1$ is selected from the hydrolyzable groups consisting of —Cl, —Br, —OH, —OR$^3$, R$^3$C(=O)O—, —O—N=CR$^3$$_2$, and (—O—)$_{0.5}$;

Z$^2$ and Z$^3$ are independently selected from the group consisting of hydrogen, the members listed above for R$^3$, and the members listed above for Z$^1$;

at least one occurrence of $Z^1$, $Z^2$, and $Z^3$ in Formula 7 is $(-O-)_{0.5}$;

$C_6H_9$ in Formula 8 represents any cyclohexane fragment obtainable by removal of three hydrogen atoms from a cyclohexane molecule;

$N_3C_3O_3$ in Formula 9 represents N,N',N''-trisubstituted cyanurate.

a is 0 to 7;
b is 1 to 3;
c is 1 to 6, preferably 1 to 4;
d is 1 to r;
j is 0 or 1, but it may be 0 if, and only if, p is 1;
k is 1 to 2;
p is 0 to 5;
q is 0 to 6;
r is 1 to 3;
s is 1 to 3;
t is 0 to 5;
x is 2 to 20;
z is 0 to 2;
provided that:
(a) if A is carbon, sulfur, or sulfonyl, then
  (i) a+b is 2, and
  (ii) k is 1;
(b) if A is phosphorus, then a+b is 3 unless both
  (i) c is greater than 1, and
  (ii) b is 1,
  in which case a is c+1; and
c) if A is phosphorus, then k is 2.

As used herein, the notation, $(-O-)_{0.5}$, refers to one half of a siloxane bond. It is used in conjunction with a silicon atom and is taken to mean one half of an oxygen atom, namely, the half bound to the particular silicon atom. It is understood that the other half of the oxygen atom and its bond to silicon occurs somewhere else in the overall molecular structure being described. Thus, the $(-O-)_{0.5}$ siloxane groups serve as the "glue" that holds the six W components of Formula 1 together. Thus, each of the l+m+y+u+v+w W components of Formula 1 needs to have at least one $(-O-)_{0.5}$ group, shared with a silicon of another W group, for it to be a part of the overall structure, but each of these components is also free to have additional $(-O-)_{0.5}$ groups, up to the total number of hydrolyzable groups present. Moreover, the additional $(-O-)_{0.5}$ groups can each be, independently of the rest, bridged to another W group, or internal. An internal $(-O-)_{0.5}$ group is one that would bridge silicon atoms within a single W group, and could occur within a single W group if it contained more than one silicon atom.

Representative examples of the functional groups (—YS—) present in the hydrolyzable blocked mercaptosilane silane fragments of the present invention include thiocarboxylate ester, —C(=O)—S—; dithiocarboxylate, —C(=S)—S—; thiocarbonate ester, —O—C(=O)—S—; dithiocarbonate ester, —S—C(=O)—S— and —O—C(=S)—S—; trithiocarbonate ester, —S—C(=S)—S—; thiocarbamate ester, (—N—)C(=O)—S; dithiocarbamate ester, (—N—)C(=S)—S—; thiosulfonate ester, —S(=O)₂—S—; thiosulfate ester, —O—S(=O)₂—S—; thiosulfamate ester, (—N—)S(=O)₂—S—; thiosulfinate ester, —S(=O)—S—; thiosulfite ester, —O—S(=O)—S—; thiosulfimate ester, (—N—)S(=O)—S—; thiophosphate ester, P(=O)(O—)₂(S—); dithiophosphate ester, P(=O)(O—)(S—)₂ or P(=S)(O—)₂(S—); trithiophosphate ester, P(=O)(S—)₃ or P(=S)(O—)(S—)₂; tetrathiophosphate ester P(=S)(S—)₃; thiophosphamate ester, —P(=O)(—N—)(S—); dithiophosphamate ester, —P(=S)(—N—)(S—); thiophosphoramidate ester, (—N—)P(=O)(O—)(S—); dithiophosphoramidate ester, (—N—)P(=O)(S—)₂ or (—N—)P(=S)(O—)(S—); and trithiophosphoramidate ester, (—N—)P(—S)(S—)₂.

Preferred hydrolyzable blocked mercaptosilane silane fragments of the present invention are those wherein the Y groups are —C(=NR)—; —SC(=NR)—; —SC(=O)—; —OC(=O)—; —S(=O)—; —S(=O)₂—; —OS(=O)₂—; —(NR)S(=O)₂—; —SS(=O)—; —OS(=O)—; —(NR)S(=O)—; —SS(=O)₂—; (—S)₂P(=O)—; —(—S)P(=O)—; —P(=O)(—)₂; (—S)₂P(=S)—; —(—S)P(=S)—; —P(=S)(—)₂; (—NR)₂P(=O)—; (—NR)(—S)P(=O)—; (—O)(—NR)P(=O)—; (—O)(—S)P(=O)—; (—O)₂P(=O)—; —(—O)P(=O)—; —(—NR)P(=O)—; (—NR)₂P(=S)—; (—NR)(—S)P(=S)—; (—O)(—NR)P(=S)—; (—O)(—S)P(=S)—; (—O)₂P(=S)—; —(—O)P(=S)—; and —(—NR)P(=S)—. Particularly preferred are —OC(=O)—; —SC(=O)—; —S(=O)—; —OS(=O)—; —(—S)P(=O)—; and —P(=O)(—)₂.

Another preferred hydrolyzable blocked mercaptosilane silane fragment would be one wherein Y is RC(=O)— in which R has a primary carbon attached to the carbonyl and is a $C_2$-$C_{12}$ alkyl, more preferably a $C_6$-$C_8$ alkyl.

Another preferred structure is of the form $X_3SiGSC(=O)GC(=O)SGSiX_3$ wherein G is a divalent hydrocarbon. Examples of G include —(CH$_2$)$_n$— wherein n is 1 to 12, diethylene cyclohexane, 1,2,4-triethylene cyclohexane, and diethylene benzene. It is preferred that the sum of the carbon atoms within the G groups within the molecule are from 3 to 18, more preferably 6 to 14. This amount of carbon in the blocked mercaptosilane facilitates the dispersion of the inorganic filler into the organic polymers, thereby improving the balance of properties in the cured filled elastomer.

Preferable R groups are hydrogen, $C_6$ to $C_{10}$ aryl, and $C_1$ to $C_6$ alkyl.

Specific examples of X are methoxy, ethoxy, propoxy, isopropoxy, isobutoxy, acetoxy, and oximato. Methoxy, ethoxy, and acetoxy are preferred. At least one X must be reactive, i.e., hydrolyzable and at least one occurrence of X must be $(-O-)_{0.5}$, i.e., part of a siloxane bond.

In preferred embodiments, p is 0 to 2; X is RO— or RC(=O)O—; R is hydrogen, phenyl, isopropyl, cyclohexyl, or isobutyl; and G is a substituted phenyl or substituted straight chain $C_2$ to $C_{12}$ alkyl. The most preferred embodiments include those wherein p is zero, X is ethoxy, and G is a $C_3$-$C_{12}$ alkyl derivative.

Representative examples of the hydrolyzable blocked mercaptosilane silane fragments of the present invention include those whose parent silanes are 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldietboxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-

4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5-triethoxysilylpentyl)benzoic acid; 6-triethoxysilyl-1-hexyl thioacetate; 1-triethoxysiiyl-5-hexyl thioacetate; 8-triethoxysilyl-1-octyl thioacetate; 1-triethoxysilyl-7-octyl thioacetate; 6-triethoxysilyl-1-hexyl thioacetate;, 1-triethoxysilyl-5-octyl thioacetate; 8-trimethoxysilyl-4-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctoate; 3-triethoxysilyl-1-propyl thiopalmitate; 3-triethoxysilyl-1-propyl thiooctoate; 3-triethoxysilyl-1-propyl thiobenzoate; 3-triethoxysilyl-1-propyl thio-2-ethylhexanoate; 3-methyldiacetoxysilyl-1-propyl thioacetate; 3-triacetoxysilyl-1-propyl thioacetate; 2-methyldiacetoxysilyl-1-ethyl thioacetate; 2-triacetoxysilyl-1-ethyl thioacetate; 1-methyldiacetoxysilyl-1-ethyl thioacetate; 1-triacetoxysilyl-1-ethyl thioacetate; tris-(3-triethoxysilyl-1-propyl)trithiophosphate; bis-(3-triethoxysilyl-1propyl)methyldithiophosphonate; bis-(3-triethoxysilyl-1-propyl)ethyldithiophosphonate; 3-triethoxysilyl-1-propyldimethylthiophosphinate; 3-triethoxysilyl-1-propyldiethylthiophosphinate; tris-(3-triethoxysilyl-1-propyl)tetrathiophosphate; bis-(3-triethoxysilyl-1-propyl)methyltrithiophosphonate; bis-(3-triethoxysilyl-1-propyl)ethyltrithiophosphonate; 3-triethoxysilyl-1-propyldimethyldithiophosphinate; 3-triethoxysilyl-1-propyldiethyldthiophosphinate; tris-(3-methyldimethoxysilyl-1-propyl)trithiophosphate; bis-(3-methyldimethoxysilyl-1-propyl)methyldithiophosphonate; bis-(3-methyldimethoxysilyl-1-propyl)ethyldithiophosphonate; 3-methyldimethoxysilyl-1-propyldimethylthiophosphinate; 3-methyldimethoxysilyl-1-propyldiethylthiophosphinate; 3-triethoxysilyl-1-propylmethylthiosulphate; 3-triethoxysilyl-1-propylmethanethiosulphonate; 3-triethoxysilyl-1-propylethanethiosulphonate; 3-triethoxysilyl-1-propylbenzenethiosulpbonate; 3-triethoxysilyl-1-propyltoluenethiosulphonate; 3-triethoxysilyl-1-propylnaphthalenethiosulphonate; 3-triethoxysilyl-1-propylxylenethiosulphonate; triethoxysilylmethylmethylthiosulphate; triethoxysilylmethylmethanethiosulphonate; triethoxysilylmethylethanethiosulphonate; triethoxysilylmethylbenzenethiosulphonate; triethoxysilylmethyltoluenethiosulphonate; triethoxysilylmethylnaphthalenethiosulphonate; triethoxysilylmethylxylenethiosulphonate.

Representative examples of $X^1$, $Y^1$, and $Z^1$ include methoxy, ethoxy, propoxy, isopropoxy, butoxy, phenoxy, benzyloxy, hydroxy, chloro, and acetoxy. Methoxy, ethoxy, and isopropoxy are preferred. Ethoxy is most preferred.

Representative examples of $X^2$, $X^3$, $Y^2$, $Y^3$, $Z^2$, and $Z^3$ include the representative examples listed above for $X^1$ as well as hydrogen, methyl, ethyl, propyl, isopropyl, sec-butyl, phenyl, vinyl, cyclohexyl, and higher, e.g., $C_4$-$C_{20}$, straight-chain alkyl, such as butyl, hexyl, octyl, lauryl, and octadecyl. Methoxy, ethoxy, isopropoxy, methyl, ethyl, phenyl, and the higher straight-chain alkyls are preferred. Ethoxy, methyl, and phenyl are most preferred.

Preferred embodiments also include those in which $X^1$, $X^2$, and $X^3$; $Y^1$, $Y^2$, and $Y^3$; and $Z^1$, $Z^2$, and $Z^3$ are the same alkoxy group, preferably methoxy, ethoxy, or isopropoxy; more preferably, ethoxy.

Representative examples of $G^1$ include the terminal straight-chain alkyls further substituted terminally at the other end, such as $—CH_2—$, $—CH_2CH_2—$, $—CH_2CH_2CH_2—$, and $—CH_2CH_2CH_2CH_2CH_2CH_2CH_2CH_2—$, and their beta-substituted analogs, such as $—CH_2(CH_2)_mCH(CH_3)—$, where m is zero to 17; $—CH_2CH_2C(CH_3)_2CH_2—$; the structure derivable from methallyl chloride, $—CH_2CH(CH_3)CH_2—$; any of the structures derivable from divinylbenzene, such as $—CH_2CH_2(C_6H_4)CH_2CH_2—$ and $—CH_2CH_2(C_6H_4)CH(CH_3)—$, where the notation $C_6H_4$ denotes a disubstituted benzene ring; any of the structures derivable from butadiene, such as $—CH_2CH_2CH_2CH_2—$, $—CH_2CH_2CH(CH_3)—$, and $—CH_2CH(CH_2CH_3)—$; any of the structures derivable from piperylene, such as $—CH_2CH_2CH_2CH(CH_3)—$, $—CH_2CH_2CH(CH_2CH_3)—$, and $—CH_2CH(CH_2CH_2CH_3)—$; any of the structures derivable from isoprene, such as $—CH_2CH(CH_3)CH_2CH_2—$, $—CH_2CH(CH_3)CH(CH_3)—$, $—CH_2C(CH_3)(CH_2CH_3)—$, $—CH_2CH_2CH(CH_3)CH_2—$, $—CH_2CH_2C(CH_3)_2—$, and $—CH_2CH\{CH(CH_3)_2\}—$; any of the isomers of $—CH_2CH_2$-norbornyl- or $—CH_2CH_2$-cyclohexyl-; any of the diradicals obtainable from norbornane, cyclohexane, cyclopentane, tetrahydrodicyclopentadiene, or cyclododecene by loss of two hydrogen atoms; the structures derivable from limonene, $—CH_2CH(4\text{-methyl-1-}C_6H_9—)CH_3$, where the notation $C_6H_9$ denotes isomers of the trisubstituted cyclohexane ring lacking substitution in the 2 position; any of the monovinyl-containing structures derivable from trivinylcyclohexane, such as $—CH_2CH_2(\text{vinyl}C_6H_9)CH_2CH_2—$ and $—CH_2CH_2(\text{vinyl}C_6H_9)CH(CH_3)—$, where the notation $C_6H_9$ denotes any isomer of the trisubstituted cyclohexane ring; any of the monounsaturated structures derivable from myrcene containing a trisubstituted C=C, such as $—CH_2CH\{CH_2CH_2CH=C(CH_3)_2\}CH_2CH_2—$, $—CH_2CH\{CH_2CH_2CH=C(CH_3)_2\}CH(CH_3)—$, $—CH_2C\{CH_2CH_2CH=C(CH_3)_2\}(CH_2CH_3)—$, $—CH_2CH_2CH\{CH_2CH_2CH=C(CH_3)_2\}CH_2—$, $—CH_2CH_2(C—)(CH_3)\{CH_2CH_2CH=C(CH_3)_2\}$, and $—CH_2CH\{CH(CH_3)[CH_2CH_2CH=C(CH_3)_2]\}—$; and any of the monounsaturated structures derivable from myrcene lacking a trisubstituted C=C, such as $—CH_2CH(CH=CH_2)CH_2CH_2C_2C(CH_3)_2—$, $—CH_2CH(CH=CH_2)CH_2CH_2CH\{CH(CH_3)_2\}—$, $—CH_2C(=CH—CH_3)CH_2CH_2CH_2C(CH_3)_2—$, $—CH_2C(=CH—CH_3)CH_2CH_2CH\{CH(CH_3)_2\}—$, $—CH_2CH_2C(=CH_2)CH_2CH_2CH_2C(CH_3)_2—$, $—CH_2CH_2C(=CH_2)CH_2CH_2CH\{CH(CH_3)_2\}—$, $—CH_2CH=C(CH_3)_2CH_2CH_2CH_2C(CH_3)_2—$, and $—CH_2CH=C(CH_3)_2CH_2CH_2CH\{CH(CH_3)_2\}$. The preferred structures for $G^1$ are $—CH_2—$, $—CH_2CH_2—$, $—CH_2CH_2CH_2—$, $CH_2CH(CH_3)CH_2—$, and any of the diradicals obtained by 2,4 or 2,5 disubstitution of the norbornane-derived structures listed above. $—CH_2CH_2CH_2—$ is most preferred.

Representative examples of $R^2$ include methyl, vinyl, ethyl, propyl, allyl, butyl, methallyl, pentyl, hexyl, phenyl, tolyl, benzyl, octyl, xylyl, mesityl, decyl, dodecyl, hexadecyl, octadecyl, and the like. Methyl, vinyl, propyl, phenyl, octyl, and octadecyl are preferred.

Representative examples of J include the terminal straight-chain alkyls further substituted terminally at the other end, such as $—CH_2CH_2—$, $—CH_2CH_2CH_2—$, and $—CH_2CH_2CH_2CH_2CH_2CH_2CH_2CH_2—$; $—CH_2CH_2C$ (CH$_3$)$_2$CH$_2$—; the divinylbenzene derivative, —CH$_2$CH$_2$(C$_6$H$_4$)CH$_2$CH$_2$—, wherein the notation C$_6$H$_4$ denotes a disubstituted benzene ring; the butadiene derivative, —CH$_2$CH$_2$CH$_2$CH$_2$—; the isoprene derivative, —CH$_2$CH(CH$_3$)CH$_2$CH$_2$—; any of the isomers of —CH$_2$CH$_2$-norbornyl-, and —CH$_2$CH$_2$-cyclohexyl-; any of the monovinyl-containing structures derivable from trivinylcyclohexane, including the isomers of —CH$_2$CH$_2$(vinylC$_6$H$_9$)CH$_2$CH$_2$—, where the notation C$_6$H$_9$ denotes any isomer of the trisubstituted cyclohexane ring; and any of the monounsaturated structures derivable from myrcene, such as —CH$_2$CH[CH$_2$CH$_2$CH=C(CH$_3$)$_2$]CH$_2$CH$_2$— and —CH$_2$CH$_2$CH[CH$_2$CH$_2$CH=C(CH$_3$)$_2$]CH$_2$—. The preferred structures for J are —CH$_2$CH$_2$—, —CH$_2$(CH$_2$)$_p$CH$_2$— (in which p is an even integer of from 2 to 18), and any of the diradicals obtained by 2,4 or 2,5 disubstitution of the norbornane-derived structures listed above. —CH$_2$CH$_2$— is most preferred.

As used herein, the term "alkyl" includes straight, branched, and cyclic alkyl groups; the term "alkenyl" includes any straight, branched, or cyclic alkenyl group containing one or more carbon-carbon double bonds, where the point of substitution can be either at a carbon-carbon double bond or elsewhere in the group; and the term "alkynyl" includes any straight, branched, or cyclic alkynyl group containing one or more carbon-carbon triple bonds and, optionally, also one or more carbon-carbon double bonds as well, where the point of substitution can be either at a carbon-carbon triple bond, a carbon-carbon double bond, or elsewhere in the group.

Specific examples of alkyls include methyl, ethyl, propyl, isobutyl, and the like. Specific examples of alkenyls include vinyl, propenyl, allyl, methallyl, ethylidenyl norbornane, ethylidene norbornyl, ethylidenyl norbornene, ethylidene norbornenyl, and the like. Specific examples of alkynyls include acetylenyl, propargyl, methylacetylenyl, and the like.

As used herein, the term "aryl" includes any aromatic hydrocarbon from which one hydrogen atom has been removed; the term "aralkyl" includes any of the aforementioned alkyl groups in which one or more hydrogen atoms has been substituted by the same number of like and/or different aryl (as defined herein) substituents; and the term "arenyl" includes any of the aforementioned aryl groups in which one or more hydrogen atoms have been substituted by the same number of like and/or different alkyl (as defined herein) substituents.

Specific examples of aryls include phenyl, naphthalenyl, and the like. Specific examples of aralkyls include benzyl, phenethyl, and the like. Specific examples of arenyls include tolyl, xylyl, and the like.

As used herein, the terms "cyclic alkyl", "cyclic alkenyl", and "cyclic alkynyl" also include bicyclic, tricyclic, and higher cyclic structures, as well as the aforementioned cyclic structures further substituted with alkyl, alkenyl, and/or alkynyl groups. Representative examples include norbornyl, norbornenyl, ethylnorbornyl, ethylnorbornenyl, ethylcyclohexyl, ethylcyclohexenyl, cyclohexylcyclohexyl, cyclododecatrienyl, and the like.

Preparation of Silanes

The blocked mercaptosilane condensates described herein are most easily prepared by hydrolysis and condensation of blocked mercaptosilanes in the presence of the other hydrolyzable silane types described above. Water can be added as such, or prepared by an appropriate in situ technique. Acid or base catalysts can be added to increase the rate of product formation.

The blocked mercaptosilane condensates can be prepared in a single hydrolysis/condensation step or in several such steps carried out in any combination sequentially and/or in parallel. Thus, a single step method would involve the addition of water to a blend of the hydrolyzable silanes desired in the final product. Alternatively, intermediate compositions could be prepared by the stepwise addition of water to separate individual blends of hydrolyzable silanes, optionally also containing previously prepared hydrolyzates and/or condensates. The intermediate compositions could then be used in subsequent hydrolysis/condensation steps until the final desired composition is obtained.

An example of an in situ technique for the generation of water involves the reaction of formic acid with an alkoxysilane. In this method, a formate ester and water are produced. The water then reacts further to hydrolyze and condense the hydrolyzable silanes, forming the siloxane bonds.

The blocked mercaptosilane condensates can also be prepared directly from condensates of silanes that represent appropriate starting materials for the blocked mercaptosilanes, using analogous techniques that are useful for the preparation of the blocked mercaptosilanes. Thus, the preparations employed for the syntheses of the blocked mercaptosilanes would be used, but with the substitution of condensates of the hydrolyzable silane starting materials for the silane starting materials used in the original syntheses of the blocked mercaptosilanes. These synthetic techniques are described extensively and in detail in U.S. application Ser. No. 09/284,841 filed Apr. 21, 1999.

Specifically, the methods of preparation for blocked mercaptosilanes can involve esterification of sulfur in a sulfur-containing silane and direct incorporation of the thioester group in a silane, either by substitution of an appropriate leaving group or by addition across a carbon-carbon double bond. Illustrative examples of synthetic procedures for the preparation of thioester silanes would include:

Reaction 1) the reaction between a mercaptosilane and an acid anhydride corresponding to the thioester group present in the desired product;

Reaction 2) reaction of an alkali metal salt of a mercaptosilane with the appropriate acid anhydride or acid halide;

Reaction 3) the transesterification between a mercaptosilane and an ester, optionally using any appropriate catalyst such as an acid, base, tin compound, titanium compound, transition metal salt, or a salt of the acid corresponding to the ester;

Reaction 4) the transesterification between a thioester silane and another ester, optionally using any appropriate catalyst such as an acid, base, tin compound, titanium compound, transition metal salt, or a salt of the acid corresponding to the ester;

Reaction 5) the transesterification between a 1-sila-2-thiacyclopentane or a 1-sila-2-thiacyclohexane and an ester, optionally using any appropriate catalyst such as an acid, base, tin compound, titanium compound, transition metal salt, or a salt of the acid corresponding to the ester;

Reaction 6) the free radical addition of a thioacid across a carbon-carbon double bond of an alkene-functional silane, catalyzed by UV light, heat, or the appropriate free radical initiator wherein, if the thioacid is a thiocarboxylic acid, the two reagents are brought into contact with each other in such a way as to ensure that whichever reagent is added to the other is reacted substantially before the addition proceeds; and Reaction 7) the reaction between an alkali metal salt of a thioacid with a haloalkylsilane.

Acid halides include but are not limited to, in addition to organic acid halides, inorganic acid halides such as $POT_3$, $SOT_2$, $SO_2T_2$, $COT_2$, $CST_2$, $PST_3$ and $PT_3$, wherein T is a halide. Acid anhydrides include but are not limited to, in addition to organic acid anhydrides (and their sulfur analogs), inorganic acid anhydrides such as $SO_3$, $SO_2$, $P_2O_3$, $P_2S_3$, $H_2S_2O_7$, $CO_2$, COS, and $CS_2$.

Illustrative examples of synthetic procedures for the preparation of thiocarboxylate-functional silanes would include:

Reaction 8) the reaction between a mercaptosilane and a carboxylic acid anhydride corresponding to the thiocarboxylate group present in the desired product;

Reaction 9) reaction of an alkali metal salt of a mercaptosilane with the appropriate carboxylic acid anhydride or acid halide;

Reaction 10) the transesterification between a mercaptosilane and a carboxylate ester, optionally using any appropriate catalyst such as an acid, base, tin compound, titanium compound, transition metal salt, or a salt of the acid corresponding to the carboxylate ester;

Reaction 11) the transesterification between a thiocarboxylate-functional silane and another ester, optionally using any appropriate catalyst such as an acid, base, tin compound, titanium compound, transition metal salt, or a salt of the acid corresponding to the other ester;

Reaction 12) the transesterification between a 1-sila-2-thiacyclopentane or a 1-sila-2-thiacyclohexane and a carboxylate ester, optionally using any appropriate catalyst such as an acid, base, tin compound, titanium compound, transition metal salt, or a salt of the acid corresponding to the carboxylate ester;

Reaction 13) the free radical addition of a thiocarboxylic acid across a carbon-carbon double bond of an alkene-functional silane, catalyzed by UV light, heat, or the appropriate free radical initiator; and Reaction 14) the reaction between an alkali metal salt of a thiocarboxylic acid with a haloalkylsilane.

Reactions 1 and 8 can be carried out by distilling a mixture of the mercaptosilane and the acid anhydride and, optionally, a solvent. Appropriate boiling temperatures of the mixture are in the range of 50° to 250° C., preferably 60° to 200° C., more preferably 70° to 170° C. This process leads to a chemical reaction in which the mercapto group of the mercaptosilane is esterified to the thioester silane analog with release of an equivalent of the corresponding acid. The acid typically is more volatile than the acid anhydride. The reaction is driven by the removal of the more volatile acid by distillation. For the more volatile acid anhydrides, such as acetic anhydride, the distillation preferably is carried out at atmospheric pressure to reach temperatures sufficient to drive the reaction toward completion. For less volatile materials, solvents, such as toluene, xylene, glyme, and diglyme, could be used with the process to limit temperature. Alternatively, the process could be run under reduced pressure. It would be useful to use up to a twofold excess or more of the acid anhydride, which would be distilled out of the mixture after all of the more volatile reaction co-products, comprising acids and nonsilane esters, have been distilled out. This excess of acid anhydride would serve to drive the reaction to completion, as well as to help drive the co-products out of the reaction mixture. At the completion of the reaction, distillation should be continued to drive out the remaining acid anhydride. Optionally, the product could be distilled.

Reactions 2 and 9 can be carried out in two steps.

The first step would involve conversion of the mercaptosilane to a corresponding metal derivative. Alkali metal derivatives, especially sodium, but also potassium and lithium, are preferable. The alkali metal derivative would be prepared by adding the alkali metal or a strong base derived from the alkali metal to the mercaptosilane. The reaction would occur at ambient temperature. Appropriate bases would include alkali metal alkoxides, amides, hydrides, and mercaptides. Alkali metal organometallic reagents would also be effective. Grignard reagents would yield magnesium derivatives, which would be another alternative. Solvents, such as toluene, xylene, benzene, aliphatic hydrocarbons, ethers, and alcohols, could be used to prepare the alkali metal derivatives. Once the alkali metal derivative is prepared, any alcohol present must be removed. This could be done by distillation or evaporation. Alcohols, such as methanol, ethanol, propanol, isopropanol, butanol, isobutanol, and t-butanol, may be removed by azeotropic distillation with benzene, toluene, xylene, or aliphatic hydrocarbons. Toluene and xylene are preferred; toluene is most preferred.

The second step in the overall process would be to add to this solution, with stirring, the acid chloride or acid anhydride at temperatures between −20° C. and the boiling point of the mixture, preferably at temperatures between 0° C. and ambient temperature. The product would be isolated by removing the salt and solvent. It could be purified by distillation.

Reactions 3 and 10 could be carried out by distilling a mixture of the mercaptosilane and the ester and, optionally, a solvent and/or a catalyst. Appropriate boiling temperatures of the mixture would be above 100° C. This process leads to a chemical reaction in which the mercapto group of the mercaptosilane is esterified to the thioester silane analog with release of an equivalent of the corresponding alcohol. The reaction is driven by the removal of the alcohol by distillation, either as the more volatile species, or as an azeotrope with the ester. For the more volatile esters, the distillation is suitably carried out at atmospheric pressure to reach temperatures sufficient to drive the reaction toward completion. For less volatile esters, solvents, such as toluene, xylene, glyme, and diglyme, could be used with the process to limit temperature. Alternatively, the process could be run at reduced pressure. It is useful to use up to a twofold excess or more of the ester, which would be distilled out of the mixture after all of the alcohol co-product has been distilled out. This excess ester would serve to drive the reaction to completion as well as to help drive the co-product alcohol out of the reaction mixture. At the completion of the reaction, distillation would be continued to drive out the remaining ester. Optionally, the product could be distilled.

Reactions 4 and 11 could be carried out by distilling a mixture of the thioester silane and the other ester and, optionally, a solvent and/or a catalyst. Appropriate boiling temperatures of the mixture would be above 80° C.; preferably above 100° C. The temperature would preferably not exceed 250° C. This process leads to a chemical reaction in which the thioester group of the thioester silane is transesterified to a new thioester silane with release of an equivalent of a new ester. The new thioester silane generally would be the least volatile species present. However, the new ester would be more volatile than the other reactants. The reaction would be driven by the removal of the new ester by distillation. The distillation can be carried out at atmospheric pressure to reach temperatures sufficient to drive the reaction toward completion. For systems containing only less volatile materials, solvents, such as toluene, xylene, glyme, and diglyme, could be used with the process to limit temperature. Alternatively, the process could be run at reduced pressure. It would be useful to use up to a twofold excess or more of the other ester, which would be distilled out of the mixture after all of the new ester co-product has been distilled out. This excess other ester would serve to drive the reaction to completion as well as to help drive the co-product other ester out of the reaction mixture. At the completion of the reaction, distillation would be continued to drive out the remaining new ester. Optionally, the product then could be distilled.

Reactions 5 and 12 could be carried out by heating a mixture of the 1-sila-2-thiacyclopentane or the 1-sila-2-thiacyclohexane and the ester with the catalyst. Optionally, the mixture could be heated or refluxed with a solvent, preferably a solvent whose boiling point matches the desired temperature. Optionally, a solvent of higher boiling point than the desired reaction temperature can be used at reduced pressure, the pressure being adjusted to bring the boiling point down to the desired reaction temperature. The temperature of the mixture would be in the range of 80° to 250° C.; preferably 100° to 200° C. Solvents, such as toluene, xylene, aliphatic hydrocarbons, and diglyme, could be used with the process to adjust the temperature. Alternatively, the process could be run under reflux at reduced pressure. The most preferred condition is to heat a mixture of the 1-sila-2-thiacyclopentane or the 1-sila-2-thiacyclohexane and the ester without solvent, preferably under an inert atmosphere, for a period of 20 to 100 hours at a temperature of 120° to 170° C. using the sodium, potassium, or lithium salt of the acid corresponding to the ester as a catalyst. The process leads to a chemical reaction in which the sulfur-silicon bond of the 1-sila-2-thiacyclopentane or the 1-sila-2-thiacyclohexane is transesterified by addition of the ester across said sulfur-silicon bond. The product is the thioester silane analog of the original 1-sila-2-thiacyclopentane or the 1-sila-2-thiacyclohexane. Optionally, up to a twofold excess or more of the ester would be used to drive the reaction toward completion. At the completion of the reaction, the excess ester can be removed by distillation. Optionally, the product could be purified by distillation.

Reactions 6 and 13 can be carried out by heating or refluxing a mixture of the alkene-functional silane and the thioacid. Aspects of Reaction 13 have been disclosed previously in U.S. Pat. No. 3,692,812 and by G. A. Gornowicz et al., in *J. Org. Chem.* (1968), 33(7), 2918-24. The uncatalyzed reaction can occur at temperatures as low as 105° C., but often fails. The probability of success increases with temperature and becomes high when the temperature exceeds 160° C. The reaction may be made reliable and the reaction brought largely to completion by using UV radiation or a catalyst. With a catalyst, the reaction can be made to occur at temperatures below 90° C. Appropriate catalysts are free radical initiators, e.g., peroxides, preferably organic peroxides, and azo compounds.

Examples of peroxide initiators include peracids, such as perbenzoic and peracetic acids; esters of peracids; hydroperoxides, such as t-butyl hydroperoxide; peroxides, such as di-t-butyl peroxide; and peroxy-acetals and ketals, such as 1,1-bis(t-butylperoxy)cyclohexane; or any other peroxide.

Examples of azo initiators include azobisisobutyronitrile (AIBN), 1,1-azobis(cyclohexanecarbonitrile) (VAZO, DuPont product), and azo-tert-butane. The reaction can be run by heating a mixture of the alkene-functional silane and the thioacid with the catalyst. It is preferred that the overall reaction be run on an equimolar or near equimolar basis to get the highest conversions. The reaction is sufficiently exothermic that it tends to lead to a rapid temperature increase to reflux followed by a vigorous reflux as the reaction initiates and continues rapidly. This vigorous reaction can lead to hazardous boil-overs for larger quantities. Side reactions, contamination, and loss in yield can result as well from uncontrolled reactions. The reaction can be controlled effectively by adding partial quantities of one reagent to the reaction mixture, initiating the reaction with the catalyst, allowing the reaction to run its course largely to completion, and then adding the remains of the reagent, either as a single addition or as multiple additives. The initial concentrations and rate of addition and number of subsequent additions of the deficient reagent depend on the type and amount of catalyst used, the scale of the reaction, the nature of the starting materials, and the ability of the apparatus to absorb and dissipate heat. A second way of controlling the reaction would involve the continuous addition of one reagent to the other with concomitant continuous addition of catalyst. Whether continuous or sequential addition is used, the catalyst can be added alone and/or pre-blended with one or both reagents or combinations thereof.

Two methods are preferred for reactions involving thiolacetic acid and alkene-functional silanes containing terminal carbon-carbon double bonds. The first involves initially bringing the alkene-functional silane to a temperature of 160° to 180° C., or to reflux, whichever temperature is lower. The first portion of thiolacetic acid is added at a rate so as to maintain up to a vigorous, but controlled, reflux. For alkene-functional silanes with boiling points above 100° to 120° C., this reflux results largely from the relatively low boiling point of thiolacetic acid (88° to 92° C., depending on purity) relative to the temperature of the alkene-functional silane. At the completion of the addition, the reflux rate rapidly subsides. It often accelerates again within several minutes, especially if an alkene-functional silane with a boiling point above 120° C. is used, as the reaction initiates. If it does not initiate within 10 to 15 minutes, initiation can be brought about by addition of catalyst. The preferred catalyst is di-t-butyl peroxide. The appropriate quantity of catalyst is from 0.2 to 2 percent, preferably from 0.5 to 1 percent, of the total mass of mixture to which the catalyst is added. The reaction typically initiates within a few minutes as evidenced by an increase in reflux rate. The reflux temperature gradually increases as the reaction proceeds. Then, the next portion of thiolacetic acid is added, and the aforementioned sequence of steps is repeated. The preferred number of thiolacetic additions for total reaction quantities of about one to about four kilograms is two, with about one-third of the total thiolacetic acid used in the first addition and the remainder in the second. For total quantities in the range of about four to ten kilograms, a total of three thiolacetic additions is preferred, the distribution being approximately 20 percent of the total used in the first addition, approximately 30 percent in the second addition, and the remainder in the third addition. For larger scales involving thiolacetic acid and alkene-functional silanes, it is preferred to use more than a total of three thiolacetic additions and more preferably, to add the reagents in the reverse order. Initially, the total quantity of thiolacetic acid is brought to reflux. This is followed by continuous addition of the alkene-functional silane to the thiolacetic acid at such a rate as to bring about a smooth but vigorous reaction rate. The catalyst, preferably di-t-butylperoxide, can be added in small portions during the course of the reaction or as a continuous flow. It is best to accelerate the rate of catalyst addition as the reaction proceeds to completion to obtain the highest yields of product for the lowest amount of catalyst required. The total quantity of catalyst used should be 0.5 percent to 2 percent of the total mass of reagents used. Whichever method is used, the reaction is followed up by a vacuum stripping process to remove volatiles and unreacted thiolacetic acid and silane. The product may be purified by distillation.

Methods to run Reactions 7 and 14 can be carried out in two steps.

The first step involves preparation of a salt of the thioacid. Alkali metal derivatives are preferred, with the sodium derivative being most preferred. These salts would be prepared as solutions in solvents in which the salt is appreciably soluble, but suspension of the salts as solids in solvents in which the salts are only slightly soluble is also a viable option. Alcohols, such as propanol, isopropanol, butanol, isobutanol, and t-butanol, and preferably methanol and ethanol are useful because the alkali metal salts are slightly soluble in them. In cases where the desired product is alkoxysilanes, it is preferable to use an alcohol corresponding to the silane alkoxy group to prevent transesterification at the silicon ester. Alternatively, nonprotic solvents can be used. Examples of appropriate solvents are ethers or polyethers, such as glyme, diglyme, and dioxanes; N'N-dimethylformamide; N'N-dimethylacetamide; dimethylsulfoxide; N-methylpyrrolidinone; or hexamethylphosphoramide.

Once a solution, suspension, or combination thereof of the salt of the thioacid has been prepared, the second step is to react it with the appropriate haloalkylsilane. This may be accomplished by stirring a mixture of the haloalkylsilane with the solution, suspension, or combination thereof of the salt of the thioacid at temperatures corresponding to the liquid range of the solvent for a period of time sufficient to complete substantially the reaction. Preferred temperatures are those at which the salt is appreciably soluble in the solvent and at which the reaction proceeds at an acceptable rate without excessive side reactions. With reactions starting from chloroalkylsilanes in which the chlorine atom is not allylic or benzylic, preferred temperatures are in the range of 60° to 160° C. Reaction times can range from one or several hours to several days. For alcohol solvents where the alcohol contains four carbon atoms or fewer, the most preferred temperature is at or near reflux. With diglyme used as a solvent, the most preferred temperature is in the range of 70° to 120° C., depending upon the thioacid salt used. If the haloalkylsilane is a bromoalkylsilane or a chloroalkylsilane in which the chlorine atom is allylic or benzylic, temperature reductions of 30° to 60° C. are appropriate relative to those appropriate for nonbenzylic or nonallylic chloroalkylsilanes because of the greater reactivity of the bromo group. Bromoalkylsilanes are preferred over chloroalkylsilanes because of their greater reactivity, lower required temperatures, and greater ease in filtration or centrifugation of the co-product alkali metal halide. This preference, however, can be overridden by the lower cost of the chloroalkylsilanes, especially for those containing the halogen in the allylic or benzylic position. For reactions between straight chain chloroalkylethoxysilanes and sodium thiocarboxylates to form thiocarboxylate ester ethoxysilanes, it is preferred to use ethanol at reflux for 10 to 20 hours if 5 percent to 20 percent mercaptosilane is acceptable in the product. Otherwise, diglyme would be an excellent choice, in which the reaction would be run preferably in the range of 80° to 120° C. for one to three hours. Upon completion of the reaction, the salts and solvent should be removed, and the product may be distilled to achieve higher purity.

If the salt of the thioacid to be used in Reactions 7 and 14 is not commercially available, it may be prepared by one of two methods, described below as Method A and Method B.

Method A involves adding the alkali metal or a base derived from the alkali metal to the thioacid. The reaction occurs at ambient temperature. Appropriate bases include alkali metal alkoxides, hydrides, carbonate, and bicarbonate. Solvents, such as toluene, xylene, benzene, aliphatic hydrocarbons, ethers, and alcohols, may be used to prepare the alkali metal derivatives.

In Method B, acid chlorides or acid anhydrides would be converted directly to the salt of the thioacid by reaction with the alkali metal sulfide or hydrosulfide. Hydrated or partially hydrous alkali metal sulfides or hydrosulfides are available. However, anhydrous or nearly anhydrous alkali metal sulfides or hydrosulfides are preferred. Hydrous materials can be used, however, but with loss in yield and hydrogen sulfide formation as a co-product. The reaction involves addition of the acid chloride or acid anhydride to the solution or suspension of the alkali metal sulfide and/or hydrosulfide and heating at temperatures ranging from ambient to the reflux temperature of the solvent for a period of time sufficiently long to complete the reaction, as evidenced by the formation of the co-product salts.

If the alkali metal salt of the thioacid is prepared in such a way that an alcohol is present, either because it was used as a solvent, or because it formed, as for example, by the reaction of a thioacid with an alkali metal alkoxide, it may be desirable to remove the alcohol if a product low in mercaptosilane is desired. In this case, it would be necessary to remove the alcohol prior to reaction of the salt of the thioacid with the haloalkylsilane. This could be done by distillation or evaporation. Alcohols, such as methanol, ethanol, propanol, isopropanol, butanol, isobutanol, and t-butanol, are preferably removed by azeotropic distillation with benzene, toluene, xylene, or aliphatic hydrocarbons. Toluene and xylene are preferred.

Use of Silanes in Elastomer

The blocked mercaptosilane condensates described herein are useful as coupling agents in mineral filled elastomer compositions as previously described for blocked mercaptosilanes. Among the advantages in the use of the blocked mercaptosilane condensates over the use of the previously described blocked mercaptosilanes are the release of less volatile organic compounds (VOC), mainly ethanol, during the elastomer compounding process, as well as a lower coupling agent loading requirement. Details of their use are analogous to those of the use of blocked mercaptosilanes, previously described in U.S. application Ser. No. 09/284,841, filed Apr. 21, 1999; U.S. Pat. No. 6,127,468; and U.S. application Ser. No. 09/736,301, filed Dec. 15, 2000.

More specifically, the blocked mercaptosilane condensates described herein are useful as coupling agents for organic polymers (e.g., elastomers) and inorganic fillers. By virtue of their use, the high efficiency of the mercapto group can be utilized without the detrimental side effects typically associated with the use of mercaptosilanes, such as high processing viscosity, less than desirable filler dispersion, premature curing (scorch), and odor. These benefits are accomplished because the mercaptan group initially is non-reactive because of the blocking group. The blocking group substantially prevents the silane from coupling to the organic polymer during the compounding of the rubber. Generally, only the reaction of the silane —$SiX_3$ group with the filler can occur at this stage of the compounding process.

Thus, substantial coupling of the filler to the polymer is precluded during mixing, thereby minimizing the undesirable premature curing (scorch) and the associated undesirable increase in viscosity. One can achieve better cured filled rubber properties, such as a balance of high modulus and abrasion resistance, because of the avoidance of premature curing.

In use, one or more of the blocked mercaptosilane condensates is mixed with the organic polymer before, during, or after the compounding of the filler into the organic polymer. It is preferred to add the silanes before or during the compounding of the filler into the organic polymer, because these silanes facilitate and improve the dispersion of the filler. The total amount of silane present in the resulting combination should be about 0.05 to about 25 parts by weight per hundred parts by weight of organic polymer (phr); more preferably 1 to 10 phr. Fillers can be used in quantities ranging from about 5 to about 100 phr, more preferably from 25 to 80 phr.

When reaction of the mixture to couple the filler to the polymer is desired, a deblocking agent is added to the mixture to deblock the blocked mercaptosilane condensate. The deblocking agent may be added at quantities ranging from about 0.1 to about 5 phr; more preferably in the range of from 0.5 to 3 phr. The deblocking agent may be a nucleophile containing a hydrogen atom sufficiently labile such that hydrogen atom could be transferred to the site of the original blocking group to form the mercaptosilane. Thus, with a blocking group acceptor molecule, an exchange of hydrogen from the nucleophile would occur with the blocking group of the blocked mercaptosilane to form the mercaptosilane and the corresponding derivative of the nucleophile containing the original blocking group. This transfer of the blocking group from the silane to the nucleophile could be driven, for example, by a greater thermodynamic stability of the products (mercaptosilane and nucleophile containing the blocking group) relative to the initial reactants (blocked mercaptosilane and nucleophile). For example, carboxyl blocking groups deblocked by amines would yield amides, sulfonyl blocking groups deblocked by amines would yield sulfonamides, sulfinyl blocking groups deblocked by amines would yield sulfinamides, phosphonyl blocking groups deblocked by amines would yield phosphonamides, phosphinyl blocking groups deblocked by amines would yield phosphinamides. What is important is that regardless of the blocking group initially present on the blocked mercaptosilane and regardless of the deblocking agent used, the initially substantially inactive (from the standpoint of coupling to the organic polymer) blocked mercaptosilane is substantially converted at the desired point in the rubber compounding procedure to the active mercaptosilane. It is noted that partial amounts of the nucleophile may be used (i.e., a stoichiometric deficiency), or even weak nucleophile, if one were to only deblock part of the blocked mercaptosilane to control the degree of vulcanization of a specific formulation.

The deblocking agent could be added in the curative package or, alternatively, at any other stage in the compounding process as a single component. Classes of compounds which would act as deblocking agents, but not normally effective as cure accelerators, allowing for selection between the two, are oxides, hydroxides, carbonates, bicarbonates, alkoxides, phenoxides, sulfanamide salts, acetyl acetonates, carbon anions derived from high acidity C—N bonds, malonic acid esters, cyclopentadienes, phenols, sulfonamides, nitrites, fluorenes, tetra-alkyl ammonium salts, and tetra-alkyl phosphonium salts.

The rubber composition need not be, but preferably is, essentially free of functionalized siloxanes, especially those of the type disclosed in Australian Patent AU-A-10082/97, which is incorporated herein by reference. Most preferably, the rubber composition is free of functionalized siloxanes.

In practice, sulfur vulcanized rubber products typically are prepared by thermomechanically mixing rubber and various ingredients in a sequentially step-wise manner followed by shaping and curing the compounded rubber to form a vulcanized product. First, for the aforesaid mixing of the rubber and various ingredients, typically exclusive of sulfur and sulfur vulcanization accelerators (collectively "curing agents"), the rubber(s) and various rubber compounding ingredients typically are blended in at least one, and often (in the case of silica filled low rolling resistance tires) two or more, preparatory thermomechanical mixing stage(s) in suitable mixers. Such preparatory mixing is referred to as non-productive mixing or non-productive mixing steps or stages. Such preparatory mixing usually is conducted at temperatures up to 140° C. to 200° C., often in the range of from 150° C. to 180° C. Subsequent to such preparatory mixing stages, in a final mixing stage, sometimes referred to as a productive mixing stage, deblocking agent (in the case of this invention), curing agents, and possibly one or more additional ingredients, are mixed with the rubber compound or composition, typically at a temperature in a range of 50° C. to 130° C., which is a lower temperature than the temperatures utilized in the preparatory mixing stages to prevent or retard premature curing of the sulfur curable rubber, which is sometimes referred to as scorching of the rubber composition. The rubber mixture, sometimes referred to as a rubber compound or composition, typically is allowed to cool, sometimes after or during a process intermediate mill mixing, between the aforesaid various mixing steps, for example, to a temperature of about 50° C. or lower. When it is desired to mold and to cure the rubber, the rubber is placed into the appropriate mold at about at least 130° C. and up to about 200° C., which will cause the vulcanization of the rubber by the mercapto groups on the mercaptosilane and any other free sulfur sources in the rubber mixture.

By thermomechanical mixing is meant that the rubber compound, or composition of rubber and rubber compounding ingredients, is mixed in a rubber mixture under high shear conditions where it autogenously heats up as a result of the mixing primarily due to shear and associated friction within the rubber mixture in the rubber mixer. Several chemical reactions may occur at various steps in the mixing and curing processes.

The first reaction is a relatively fast reaction and is considered herein to take place between the filler and the $SiX_3$ group of the blocked mercaptosilane. Such reaction may occur at a relatively low temperature, such as, for example, at about 120° C. The second and third reactions are considered herein to be the deblocking of the mercaptosilane and the reaction which takes place between the sulfuric part of the organosilane (after deblocking), and the sulfur vulcanizable rubber at a higher temperature; for example, above about 140° C.

Another sulfur source may be used; for example, in the form of elemental sulfur as $S_8$. A sulfur donor is considered herein as a sulfur-containing compound that makes sulfur available for vulcanization at a temperature of 140° C. to 190° C. Such sulfur donors may be, but are not limited to, for example, polysulfide vulcanization accelerators and organosilane polysulfides with at least two connecting sulfur atoms in its polysulfide bridge. The amount of free sulfur source addition to the mixture can be controlled or manipulated as a matter of choice relatively independent of the addition of the aforesaid blocked mercaptosilane. Thus, for example, the independent addition of a sulfur source may be manipulated by the amount of addition thereof and by the sequence of addition relative to the addition of other ingredients to the rubber mixture.

Addition of an alkyl silane to the coupling agent system (blocked mercaptosilane condensate plus additional free sulfur source and/or vulcanization accelerator) typically in a mole ratio of alkyl silane to blocked mercaptosilane condenstate in a range of 1/50 to 1/2 promotes an even better control of rubber composition processing and aging.

A rubber composition is prepared by a process that comprises the sequential steps of:
(A) thermomechanically mixing, in at least one preparatory mixing step, to a temperature of 140° C. to 200° C., alternatively to 140° C. to 190° C., for a total mixing time of 2 to 20, alternatively 4 to 15, minutes for such mixing step(s)
  (i) 100 parts by weight of at least one sulfur vulcanizable rubber selected from conjugated diene homopolymers and copolymers, and copolymers of at least one conjugated diene and aromatic vinyl compound,
  (ii) 5 to 100, preferably 25 to 80, phr (parts per hundred rubber) of particulate filler, wherein preferably the filler contains 1 to 85 weight percent carbon black, and
  (iii) 0.05 to 20 parts by weight filler of at least one blocked mercaptosilane condensate;
(B) subsequently blending therewith, in a final thermomechanical mixing step at a temperature to 50° C. to 130° C. for a time sufficient to blend the rubber, preferably between 1 and 30 minutes, more preferably 1 to 3 minutes, at least one deblocking agent at about 0.05 to 20 parts by weight of the filler and a curing agent at 0 to 5 phr; and, optionally,
(C) curing said mixture at a temperature of 130 to 200° C. for about 5 to 60 minutes.

The process may also comprise the additional steps of preparing an assembly of a tire or sulfur vulcanizable rubber with a tread comprised of the rubber composition prepared according to this invention and vulcanizing the assembly at a temperature in a range of 130° C. to 200° C.

Suitable organic polymers and fillers are well known in the art and are described in numerous texts, of which two examples include *The Vanderbilt Rubber Handbook*; R. F. Ohm, ed.; R. T. Vanderbilt Company, Inc., Norwalk, Conn.; 1990 and *Manual For The Rubber Industry*; T. Kempermann, S. Koch, J. Sumner, eds.; Bayer A. G., Leverkusen, Germany; 1993. Representative examples of suitable polymers include solution styrene-butadiene rubber (sSBR), styrene-butadiene rubber (SBR), natural rubber (NR), polybutadiene (BR), ethylene-propylene co- and ter-polymers (EP, EPDM), and acrylonitrile-butadiene rubber (NBR).

The rubber composition is comprised of at least one diene-based elastomer, or rubber. Suitable conjugated dienes are isoprene and 1,3-butadiene and suitable vinyl aromatic compounds are styrene and alpha methyl styrene. Thus, the rubber is a sulfur curable rubber.

Such diene-based elastomer, or rubber, may be selected, for example, from at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35-50 percent vinyl), high vinyl polybutadiene rubber (50-75 percent vinyl), styrene/isoprene copolymers, emulsion polymerization prepared styrene/butadiene/acrylonitrile terpolymer rubber, and butadiene/acrylonitrile copolymer rubber. An emulsion polymerization derived styrene/butadiene (eSBR) might be used having a relatively conventional styrene content of 20 to 28 percent bound styrene or, for some applications, an eSBR having a medium to relatively high bound styrene content, namely, a bound styrene content of 30 to 45 percent. Emulsion polymerization prepared styrene/butadiene/acrylonitrile terpolymer rubbers containing 2 to 40 weight percent bound acrylonitrile in the terpolymer are also contemplated as diene-based rubbers for use in this invention.

The solution polymerization prepared SBR (sSBR) typically has a bound styrene content in a range of 5 to 50, preferably 9 to 36, percent. Polybutadiene elastomer may he conveniently characterized, for example, by having at least a 90 weight percent cis-1,4-content.

Representative examples of suitable filler materials include metal oxides, such as silica (pyrogenic and precipitated), titanium dioxide, aluminosilicate and alumina, siliceous materials including clays and talc, and carbon black. Particulate, precipitated silica is also sometimes used for such purpose, particularly when the silica is used in connection with a silane. In some cases, a combination of silica and carbon black is utilized for reinforcing fillers for various rubber products, including treads for tires. Alumina can be used either alone or in combination with silica. The term "alumina" can be described herein as aluminum oxide, or $Al_2O_3$. The fillers may be hydrated or in anhydrous form. Use of alumina in rubber compositions can be shown, for example, in U.S. Pat. No. 5,116,886 and EP 631 982.

The blocked mercaptosilane may be premixed, or pre-reacted, with the filler particles or added to the rubber mix during the rubber and filler processing, or mixing stage. If the silane and filler are added separately to the rubber mix during the rubber and filler mixing, or processing stage, it is considered that the blocked mercaptosilane then combines in situ with the filler.

The vulcanized rubber composition should contain a sufficient amount of filler to contribute a reasonably high modulus and high resistance to tear. The combined weight of the filler may be as low as about 5 to 100 phr, but is more preferably from 25 to 85 phr.

Precipitated silicas are preferred as the filler. The silica may be characterized by having a BET surface area, as measured using nitrogen gas, preferably in the range of 40 to 600, and more usually in a range of 50 to 300 $m^2/g$. The silica typically may also be characterized by having a dibutylphthalate (DBP) absorption value in a range of 100 to 350, and more usually 150 to 300. Further, the silica, as well as the aforesaid alumina and aluminosilicate, may be expected to have a CTAB surface area in a range of 100 to 220. The CTAB surface area is the external surface area as evaluated by cetyl trimethylammonium bromide with a pH of 9. The method is described in ASTM D 3849. Mercury porosity surface area is the specific surface area determined by mercury porosimetry. For such technique, mercury is penetrated into the pores of the sample after a thermal treatment to remove volatiles. Set-up conditions may be suitably described as using a 100 mg sample; removing volatiles during 2 hours at 105° C. and ambient atmospheric pressure; ambient to 2000 bars pressure measuring range. Such evaluation may be performed according to the method described in Winslow, Shapiro in ASTM bulletin, p.39

(1959) or according to DIN 66133. For such an evaluation, a CARLO-ERBA Porosimeter 2000 might be used. The average mercury porosity specific surface area for the silica should be in a range of 100 to 300 m$^2$/g.

A suitable pore size distribution for the silica, alumina, and aluminosilicate according to such mercury porosity evaluation is considered herein to be: five percent or less of its pores have a diameter of less than about 10 nm; 60 to 90 percent of its pores have a diameter of 10 to 100 nm; 10 to 30 percent of its pores have a diameter at 100 to 1,000 nm; and 5 to 20 percent of its pores have a diameter of greater than about 1,000 nm.

The silica might be expected to have an average ultimate particle size, for example, in the range of 0.01 to 0.05 µm as determined by the electron microscope, although the silica particles may be even smaller, or possibly larger, in size. Various commercially available silicas may be considered for use in this invention, such as, from PPG Industries under the HI-SIL trademark with designations HI-SIL 210, 243, etc.; silicas available from Rhone-Poulenc, with, for example, designation of ZEOSIL 1165MP; silicas available from Degussa with, for example, designations VN2 and VN3, etc., and silicas commercially available from Huber having, for example, a designation of HUBERSIL 8745.

Where it is desired for the rubber composition, which contains both a siliceous filler, such as silica, alumina, and/or aluminosilicates and also carbon black reinforcing pigments, to be primarily reinforced with silica as the reinforcing pigment, it is often preferable that the weight ratio of such siliceous fillers to carbon black be at least 3/1 and preferably at least 10/1 and, thus, in a range of 3/1 to 30/1. The filler may be comprised of 15 to 95 weight percent precipitated silica, alumina, and/or aluminosilicate and, correspondingly, 85 to 5 weight percent carbon black, wherein the carbon black has a CTAB value in a range of 80 to 150. Alternatively, the filler can be comprised of 60 to 95 weight percent of said silica, alumina, and/or aluminosilicate and, correspondingly, 40 to 5 weight percent carbon black. The siliceous filler and carbon black may be pre-blended or blended together in the manufacture of the vulcanized rubber.

The rubber composition may be compounded by methods known in the rubber compounding art, such as mixing the various sulfur-vulcanizable constituent rubbers with various commonly used additive materials such as, for example, curing aids, such as sulfur, activators, retarders, and accelerators, processing additives, such as oils, resins including tackifying resins, silicas, plasticizers, fillers, pigments, fatty acid, zinc oxide, waxes, antioxidants and antiozonants, peptizing agents, and reinforcing materials, such as, for example, carbon black. Depending on the intended use of the sulfur vulcanizable and sulfur vulcanized material (rubbers), the additives mentioned above are selected and commonly used in conventional amounts.

The vulcanization may be conducted in the presence of an additional sulfur vulcanizing agent. Examples of suitable sulfur vulcanizing agents include, for example, elemental sulfur (free sulfur) or sulfur donating vulcanizing agents, for example, an amino disulfide, polymeric polysulfide, or sulfur olefin adducts which are conventionally added in the final, productive, rubber composition mixing step. The sulfur vulcanizing agents (which are common in the art) are used, or added in the productive mixing stage, in an amount ranging from 0.4 to 3 phr, or even, in some circumstances, up to about 8 phr, with a range of from 1.5 to 2.5 phr, sometimes from 2 to 2.5 phr, being preferred. Vulcanization accelerators may be used herein. It is appreciated that they may be of the type, such as, for example, benzothiazole, alkyl thiuram disulfide, guanidine derivatives, and thiocarbamates. Vulcanization accelerators may be primary or secondary accelerators and individual accelerators may function as either primary or secondary accelerators. Representative accelerators include, but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine), and dithiobis(dibenzyl amine). Other additional sulfur donors, may be, for example, thiuram and morpholine derivatives. Such donors include, but not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally and preferably, a primary accelerator is used in a total amount ranging from 0.5 to 4, preferably 0.8 to 1.5, phr. Combinations of a primary and a secondary accelerator might be used with the secondary accelerator being used in a smaller amount (of 0.05 to 3 phr) in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfenamides, dithiocarbamates, and xanthates, but the type may be influenced if the accelerant is also a deblocker. Examples of primary accelerators used in the art include N-cyclohexyl-2-benzothiazyl sulfenamide (CBS); N-t-butyl-2-benzothiazyl sulfenamide (TBBS); benzothiazyl-2-sulphene morpholide (MBS); N-dicyclohexyl-2-benzothiazyl sulfenamide (DCBS); tetramethylthiuram monosulfide (TMTM); tetramethylthiuram disulfide (TMTD); tetramethylthiuram hexasulfide; N,N-diphenylurea; and morpholinethiobenzothiazole. If a second accelerator is used, the secondary accelerator is preferably a guanidine, dithiocarbamate, or thiuram compound. Examples of secondary accelerators commonly used in the art include diphenylguanidine (DPG); tetramethylthiuram hexasulfide; mercaptobenzothiazole (MBT); mercaptobenzothiazole disulfide (MBTS); the zinc salt of mercaptobenzothiazole (ZMBT); zinc dibutyldithiocarbamate; zinc diethyldithiocarbamate; zinc dimethyldithiocarbamate; zinc dibenzyldithiocarbamate; zinc ethylphenyldithiocarbamate; nickel dibutyldithiocarbamate; copper dimethyldithiocarbamate; piperidinium pentamethylene dithiocarbamate; thiocarbanilide; 1,3-diethylthiourea-1,3-dibutylthiourea; di(pentamethylene)thiuram hexasulfide; and morpholinethiobenzothiazole. Numerous specific examples of guanidines, amines, and imines well known in the art, which are useful as components in curatives for rubber, are cited in *Rubber Chemicals*; J. Van Alphen; Plastics and Rubber Research Institute TNO, Delft, Holland; 1973.

In elastomer formulations of the present invention, it is important to consider an additional factor in the choice of the accelerator system. This factor is related to the deblocking action of the accelerator on the blocked mercaptosilane condensate. Deblocking of the blocked mercaptosilane condensate occurs by the catalytic or chemical action of a component added to the elastomer at a point where deblocking is desired. Amines or related basic substances are particularly suitable in this regard. Most of the aforementioned accelerators are amine based, but their basicity may be reduced because the nitrogen atom is bound to a sulfur atom, carbonyl, or thiocarbonyl. This influences the type of accelerator package ideally suited for elastomer compositions of the present invention. Thus, a preferred method of operation would be to use such amines as both deblocking agent and accelerator.

Among the accelerators of demonstrated suitability for use with blocked mercaptosilane condensates are diphenylguanidine (DPG) and tetramethylthiuram monosulfide (TMTM). The TMTM is preferred. It is believed that the family of such compounds, i.e., $R_2NC(=S)-S_n-C(=S)NR_2$ wherein n=1 to 4, R is an akyl group of 1 to 4 carbon atoms, would be preferred.

Free amines, or closely related chemical compounds, such as imines, anilines, and nitrogen-containing heterocycles are expected to deblock and thereby activate the blocked mercaptosilanes much more readily, rapidly, and/or completely than many of the aforementioned accelerators on the basis of their stronger basicity. Suitable amine accelerators would be secondary or tertiary amines containing substantial carbon content so that they contain sufficient hydrophobicity in their structure to offset the hydrophilicity of the basic amine group, so that dispersion into the rubber matrix is promoted. All such compounds should have boiling points of at least 140° C. and preferably greater than 200° C. This includes secondary or tertiary amines with enough carbon content to be miscible in the rubber mixture, generally about a molar ratio of C:N of at least 6:1. Alternatively, the amine may be a heterocyclic amine of the following classes: quinoline, imidazoline, imidazolidone, hydantoin, hydralazine, pyrazole, pyrazine, purine, pyrimidine, pyrrole, indole, oxazole, thiazole, benzimidazole, benzoxazole, benzothiazole, triazole, benzotriazole, tetrazole, aniline, phenylene diamine, and imine. Factors in considering the accelerators of the free amine type would, of course, be factors such as toxicity, physical state (i.e. liquid or solid), volatility, its ability to disperse into the formulation, and the like.

Most suitably, one can use mixtures of the vulcanization accelerators, which are used to deblock the silane with the aforementioned deblocking agents to control the rate and degree of rubber cure as to to deblocking and crosslinking of the silane. Each rubber mixture will have its own optimal blend which may be determined by simple experimentation.

Typical amounts of tackifier resins, if used, comprise 0.5 to 10 phr, usually 1 to 5 phr. Typical amounts of processing aids comprise 1 to 50 phr. Such processing aids can include, for example, aromatic, naphthenic, and/or paraffinic processing oils. Typical amounts of antioxidants comprise 1 to 5 phr. Representative antioxidants may be, for example, diphenyl-p-phenylenediamine and others, such as, for example, those disclosed in the *Vanderbilt Rubber Handbook* (1978), pages 344-346. Typical amounts of antiozonants, comprise 1 to 5 phr. Typical amounts of fatty acids, if used, which can include stearic acid, comprise 0.5 to 3 phr. Typical amounts of zinc oxide comprise 2 to 5 phr. Typical amounts of waxes comprise 1 to 5 phr. Often microcrystalline waxes are used. Typical amounts of peptizers comprise 0.1 to 1 phr. Typical peptizers may be, for example, pentachlorothiophenol and dibenzamidodiphenyl disulfide.

The rubber composition of this invention can be used for various purposes. For example, it can be used for various tire compounds. Such tires can be built, shaped, molded, and cured by various methods which are known and will be readily apparent to those having skill in such art.

All references cited herein are incorporated by reference to the extent they are relevant to the present invention.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

Example 1

Homogeneous Preparation of a

Condensate of 3-acetylthio-1-propyltriethoxysilane

A crude starting material of 3-acetylthio-1-propyltriethoxysilane was first purified by flash vacuum distillation from sodium ethoxide. The distillate was redistilled. An initial forecut of volatiles was discarded and the bulk of the distillate was retained as a clear and colorless liquid, which was used as the starting material for the preparation of the condensate. To a homogeneous mixture of 3-acetylthio-1-propyltriethoxysilane (74.35 grams, 0.2525 mole) and anhydrous ethanol (70 grams) was added a modest quantity of water (2.27 grams, 0.126 mole), with stirring. The mixture was allowed to stand at ambient temperature for six weeks. After this time, volatiles were removed by rotary evaporation.

Example 2

Heterogeneous Preparation of a

Condensate of 3-acetylthio-1-propyltriethoxysilane

A crude starting material of 3-acetylthio-1-propyltriethoxysilane was first purified by flash vacuum distillation from sodium ethoxide. The distillate was redistilled. An initial forecut of volatiles was discarded and the bulk of the distillate was retained as a clear and colorless liquid, which was used as the starting material for the preparation of the condensate. A two-phase mixture of 3-acetylthio-1-propyltriethoxysilane (68.3 grams, 0.232 mole) and water (49 grams, 2.7 moles) was stirred for six weeks at ambient temperature. After this time, the liquid layers were separated in a separatory funnel. Volatiles were removed by rotary evaporation from the organic phase.

Example 3

Homogeneous Preparation of a Condensate of [8-octanoylthio-1-propyltriethoxysilane]3-triethoxysilyl-1-propyl thiooctoate A quantity of [8-octanoylthio-1-propyltriethoxysilane]3-triethoxysilyl-1-propyl thiooctoate (240 grams, 0.66 mole) was added to a homogeneous mixture of anhydrous ethanol (54 grams) and water (5.93 grams, 0.329 mole) with stirring. The mixture was allowed to stand at ambient temperature for six weeks. After this time, volatiles were removed by rotary evaporation. The product was further purified by flash vacuum distilling out a forecut and retaining the nonvolatile portion of the sample. The forecut contained most of the ethyl octoate, 3-mercapto-1-propyltriethoxysilane, and 3-chloro-1-propyltriethoxysilane impurities present in the sample, as established by comparative GC (gas chromatography) with pure samples of the respective contaminants. GC analytical results (area %): Si—O—Si siloxane "dimer" of [8-octanoylthio-1-propyltriethoxysilane]3-triethoxysilyl-1-propyl thiooctoate 46.4%; [8-octanoylthio-1-propyltriethoxysilane]3-triethoxysilyl-1-propyl thiooctoate 33.0%; 1-diethoxy-1-sila-2-thiacyclopentane 0.2%; bis-3-triethoxysilyl-1-propyl disulfide 4.4%; bis-3-triethoxysilyl-1-propyl trithiocarbonate 1.0%. Higher molecular weight components of Si—O—Si siloxane "trimers", "tetramers", etc. of [8-octanoylthio-1-propyltriethoxysilane]3-triethoxysilyl-1-propyl thiooctoate are expected in these compositions, but would not have been detected by the GC spectra taken.

Example 4

Heterogeneous Preparation of a Condensate of [8-octanoylthio-1-propyltriethoxysilane]3-triethoxysilyl-1-propyl thiooctoate A two-phase mixture of [8-octanoylthio-1-propyltriethoxysilane]3-triethoxysilyl-1-propyl thiooctoate (124.3 grams, 0.3409 mole) and water (175 grams, 9.71 mole) was stirred at ambient temperature for six weeks. After this time, the liquid layers were separated in a separatory funnel. Volatiles were removed by rotary evaporation from the organic phase. The product was further purified by flash vacuum distilling out a forecut and retaining the nonvolatile portion of the sample. The forecut contained most of the ethyl octoate, 3-mercapto-1-propyltriethoxysilane, and 3-chloro-1-propyltriethoxysilane impurities present in the sample, as established by comparative GC with pure samples of the respective contaminants. GC analytical results (area %): Si—O—Si siloxane "dimer" of [8-octanoylthio-1-propyltriethoxysilane]3-triethoxysilyl-1-propyl thiooctoate 39.0%; [8-octanoylthio-1-propyltriethoxysilane]3-triethoxysilyl-1-propyl thiooctoate 37.1%; 1-diethoxy-1-sila-2-thiacyclopentane 0.4%; 3-mercapto-1-propyltriethoxysilane 0.2%; 3-ethylthio-1-propyltriethoxysilane 0.3%; bis-3-triethoxysilyl-1-propyl disulfide 5.3%; bis-3-triethoxysilyl-1-propyl trithiocarbonate 1.8%. Higher molecular weight components of Si—O—Si siloxane "trimers", "tetramers", etc. of [8-octanoylthio-1-propyltriethoxysilane]3-triethoxysilyl-1-propyl thiooctoate are expected in these compositions, but would not have been detected by the GC spectra taken.

Example 5

Heterogeneous, Acid-Catalyzed Preparation of a Condensate of [8-octanoylthio-1-propyltriethoxysilane]3-triethoxysilyl-1-propyl thiooctoate A two-phase mixture of [8-octanoylthio-1-propyltriethoxysilane]3-triethoxysilyl-1-propyl thiooctoate (125.1 grams, 0.3431 mole), water (83.4 grams, 4.63 moles), and glacial acetic acid (12.5 grams, 0.208 mole) was stirred for six weeks at ambient temperature. After this time, the liquid layers were separated in a separatory funnel. Volatiles were removed by rotary evaporation from the organic phase. The product was further purified by flash vacuum distilling out a forecut and retaining the nonvolatile portion of the sample. The forecut contained most of the ethyl octoate, 3-mercapto-1-propyltriethoxysilane, and 3-chloro-1-propyltriethoxysilane impurities present in the sample, as established by comparative GC with pure samples of the respective contaminants. GC analytical results (area %): Si—O—Si siloxane "dimer" of [8-octanoylthio-1-propyltriethoxysilane]3-triethoxysilyl-1-propyl thiooctoate 30.2%; [8-octanoylthio-1-propyltriethoxysilane]3-triethoxysilyl-1-propyl thiooctoate 50.5%; 3-mercapto-1-propyltriethoxysilane 0.2%; bis-3-triethoxysilyl-1-propyl disulfide 5.1%; bis-3-triethoxysilyl-1-propyl trithiocarbonate 1.8%. Higher molecular weight components of Si—O—Si siloxane "trimers", "tetramers", etc. of [8-octanoylthio-1-propyltriethoxysilane]3-triethoxysilyl-1-propyl thiooctoate are expected in these compositions, but would not have been detected by the GC spectra taken.

Example 6

Base-Catalyzed Preparation of a Condensate of [8-octanoylthio-1-propyltriethoxysilane]3-triethoxysilyl-1-propyl thiooctoate To the homogeneous mixture of [8-octanoylthio-1-propyltriethoxysilane]3-triethoxysilyl-1-propyl thiooctoate (72.12 grams, 0.1978 mole) and ethanol (72.3 grams) was added a modest quantity of water. The resulting mixture was stirred to a homogeneous solution, to which was subsequently added a modest quantity of water (19.6 grams, 1.09 moles). This mixture was then stirred, resulting in another homogeneous mixture. To this resulting mixture was added a small quantity of sodium ethoxide (0.086 gram, 0.0013 mole) as a 21 weight % solution (0.41 gram) in ethanol. This mixture was then stirred at ambient temperature, giving a homogeneous solution. A slight phase separation was evident in this mixture after stirring for one day. Stirring at ambient temperature was then continued for another six weeks. After this time, the liquid layers were separated in a separatory funnel. The organic was by far the predominant phase. Volatiles were removed from the organic phase by rotary evaporation. The product was further purified by flash vacuum distilling out a forecut and retaining the nonvolatile portion of the sample. The forecut contained most of the ethyl octoate, 3-mercapto-1-propyltriethoxysilane, and 3-chloro-1-propyltriethoxysilane impurities present in the sample, as established by comparative GC with pure samples of the respective contaminants. GC analytical results (area %): Si—O—Si siloxane "dimer" of [8-octanoylthio-1-propyltriethoxysilane]3-triethoxysilyl-1-propyl thiooctoate 23.6%; [8-octanoylthio-1-propyltriethoxysilane]3-triethoxysilyl-1-propyl thiooctoate 58.7%; 1-diethoxy-1-sila-2-thiacyclopentane 0.1%; 3-mercapto-1-propyltriethoxysilane 0.5%; bis-3-triethoxysilyl-1-propyl disulfide 5.1%; bis-3-triethoxysilyl-1-propyl trithiocarbonate 1.2%. Higher molecular weight components of Si—O—Si siloxane "trimers", "tetramers", etc. of [8-octanoylthio-1-propyltriethoxysilane]3-triethoxysilyl-1-propyl thiooctoate are expected in these compositions, but would not have been detected by the GC spectra taken.

Example 7

Formic Acid Catalyzed Preparation of a Condensate of [8-octanoylthio-1-propyltriethoxysilane]3-triethoxysilyl-1-propyl thiooctoate Into a one liter round bottomed flask equipped with a distillation apparatus, addition funnel, thermometer, heating mantle, and magnetic stirrer was added 200 grams (0.55 mole) of [3-octanoylthio-1-propyltriethoxysilane]3-triethoxysilyl-1-propyl thiooctoate and 1.0 gram of Purolite CT-275 dry, acidic ion exchange resin. From the addition funnel was added 12.6 grams (0.27 mole) of 96% formic acid while heating the flask contents to 80° C. with stirring. Distillation at 80° C. and 5 mm mercury vacuum, yielded 28.2 grams of low boiling components (mainly, ethanol and ethyl formate). The flask contents were filtered to yield 164.2 grams of 10 csk viscosity. Analysis by $^{29}$Si NMR indicated 2.26 ethoxy groups per Si and $^{13}$C NMR showed 2.13 ethoxy groups per Si and no loss of octanoyl groups on sulfur.

Example 8

Formic Acid Catalyzed Preparation of a Condensate of [8-octanoylthio-1-propyltriethoxysilane]3-triethoxysilyl-1-propyl thiooctoate and tetraethyl silicate Using the apparatus described in Example 7, a mixture of 364.0 grams (1.0 mole) of [3-octanoylthio-1-propyltriethoxysilane]3-triethoxysilyl-1-propyl thiooctoate, 208.3 grams (1.0 mole) of tetraethyl silicate and 2.7 grams of Purolite CT-275 ion exchange resin were added to the flask. From the addition funnel 30.6 grams water (1.7 moles) was added to the flask while the contents of the flask were heated to 55° C. The temperature was maintained at 50-55° C. for three hours with stirring. The flask was cooled to room temperature, filtered and the lower boiling components were vacuum distilled (85° C., 8 mm Hg) from the flask (mainly ethanol, 127.0 grams) to yield upon isolation 423.6 grams of an amber liquid of 14 cstk viscosity. The $^{13}$C NMR confirmed that all of the octanoyl groups remained on sulfur after this reaction.

Example 9

Formic Acid Catalyzed Preparation of a Condensate of [8-octanoylthio-1-propyltriethoxysilane]3-triethoxysilyl-1-propyl thiooctoate and octyltriethoxysilane Using the apparatus described in Example 7, a mixture of 364.0 grams (1.0 mole) of [3-octanoylthio-1-propyltriethoxysilane]3-triethoxysilyl-1-propyl thiooctoate, 276.5 grams (1.0 mole) of octyltriethoxysilane and 2.7 grams of Purolite CT-275 ion exchange resin were added to the flask. From the addition funnel 30.6 grams water (1.7 moles) was added to the flask while the contents of the flask were heated to 50° C. The temperature was maintained at 50-55° C. for two hours with stirring. The flask was cooled to room temperature, filtered, and the lower boiling components were vacuum distilled (80° C., 2 mm Hg) from the flask (mainly ethanol, 111.5 grams) to yield upon isolation 484.6 grams of an amber liquid of 14 cstk viscosity. The $^{13}$C NMR confirmed that the octanoyl groups remained on sulfur after this reaction.

Example 10

Formic Acid Catalyzed Preparation of a Condensate of [8-octanoylthio-1-propyltriethoxysilane]3-triethoxysilyl-1-propyl thiooctoate and phenyltriethoxysilane Using the apparatus described in Example 7, a mixture of 364.0 grams (1.0 mole) of [3-octanoylthio-1-propyltriethoxysilane]3-triethoxysilyl-1-propyl thiooctoate, 240.4 grams (1.0 mole) of phenyltriethoxysilane and 2.7 grams of Purolite CT-275 ion exchange resin were added to the flask. From the addition funnel 30.6 grams water (1.7 moles) was added to the flask while the contents of the flask were stirred at room temperature for 1.5 days, then were heated to 50° C. for 2 hours. The flask was cooled to room temperature, filtered, and the lower boiling components were vacuum distilled (50° C., 10 mm Hg) from the flask (mainly ethanol, 125.7 grams) to yield upon isolation 469.1 grams of an amber liquid of 14 cstk viscosity. The $^{13}$C NMR confirmed that the octanoyl groups remained on sulfur after this reaction.

Examples 11-22

In the following examples, the amounts of reactants are parts per hundred of rubber unless otherwise indicated.

The following tests were conducted with the following methods (in all examples): Mooney Viscosity @100° C. (ASTM Procedure D1646); Mooney Scorch @135° C. (ASTM Procedure D1646); Oscillating Disc Rheometer (ODR) @149° C., 1° arc, (ASTM Procedure D2084); Physical Properties, cured t90 @149° C. (ASTM Procedures D412 and D224).

Formulation: 75 Solflex 1216 sSBR, 25 Budene 1207 BR, 80 Zeosil 1165MP silica, 32.5 Sundex 3125 process oil, 2.5 Kadox 720C zinc oxide, 1.0 Industrene R stearic acid, 2.0 Santoflex 13 antiozonant, 1.5 M4067 microwax, 3.0 N330 carbon black, 1.4 Rubbermakers sulfur 104, 1.7 CBS, 2.0 DPG, and 7.2 silane.

Mixing of the formulations was carried out in a Banbury Mixer during an eight minute mixing period at 170° C. for all samples. The results of physical testing of these formulations are shown in Tables 1-(A-D). In the tables, the term "Prodex" is used, for convenience, to mean "The product of Example". Thus, for example, "Prodex 10" should be understood to mean "The product of Example 10". Where this terminology is not used, the products were made by a process analogous to that described in Example 8. Further, "Y-15099" is [8-octanoylthio-1-propyltriethoxysilane]3-triethoxysilyl-1-propyl thiooctoate and "TEOS" is tetraethoxy silane.

TABLE 1-A

| Example No. | 11 | 12 | 13 | 14 | 15 | 16 | 17 |
|---|---|---|---|---|---|---|---|
| Y-15099 | 7.2 | | | | | | |
| Prodex 10 | | 7.2 | | | | | |
| Y-15099/TEOS/oligo-merized | | | 7.2 | | | | |
| Prodex 9 | | | | 7.2 | | | |
| Prodex 7 | | | | | 7.2 | | |
| Hydrolysis Y-15099/TEOS/H$_2$O (1/1/1) | | | | | | 7.2 | |
| Hydrolysis Y-15099/TEOS/H$_2$O (1/1/1.9) | | | | | | | 7.2 |
| Mooney Viscosity @ 100° C. | | | | | | | |
| ML1 + 4 | 56 | 62 | 59 | 54 | 62 | 61 | 58 |
| Mooney Scorch @ 135° C. | | | | | | | |
| M$_v$ | 24.3 | 24.6 | 25.3 | 21.9 | 27.1 | 26.0 | 24.2 |
| MS1+, t$_3$, minutes | 8.6 | 13.4 | 10.2 | 16.4 | 9.4 | 10.1 | 9.6 |
| MS1+, t$_{18}$, minutes | 12.4 | 18.2 | 14.5 | 21.5 | 14.2 | 14.5 | 14.1 |

TABLE 1-B

| Example No. | 11 | 12 | 13 | 14 | 15 | 16 | 17 |
|---|---|---|---|---|---|---|---|
| ODR @ 149° C., 1° arc, 30 minute timer | | | | | | | |
| $M_L$ in.-lb. | 6.9 | 6.8 | 7.1 | 6.0 | 7.6 | 7.0 | 6.6 |
| $M_H$, in.-lb. | 25.8 | 29.5 | 26.5 | 27.3 | 26.9 | 27.3 | 26.1 |
| $t_{S1}$, minutes | 5.2 | 7.4 | 5.5 | 8.3 | 5.1 | 5.3 | 5.4 |
| t90, minutes | 12.4 | 15.5 | 15.5 | 17.2 | 16.2 | 15.5 | 14.2 |
| Physical Properties, cured t90 @ 149° C. | | | | | | | |
| Hardness, Shore A | 55 | 62 | 58 | 58 | 61 | 60 | 57 |
| Elongation, % | 604 | 643 | 676 | 658 | 691 | 683 | 699 |
| 25% Modulus, psi | 92 | 118 | 100 | 103 | 108 | 112 | 109 |
| 100% Modulus, psi | 218 | 275 | 218 | 234 | 224 | 225 | 227 |
| 300% Modulus, psi | 1,110 | 1,232 | 1,012 | 1,029 | 946 | 909 | 1,015 |
| Tensile, psi | 3,321 | 3,390 | 3,460 | 3,112 | 3,255 | 3,159 | 3,533 |
| 300%/25% | 12.1 | 10.4 | 10.1 | 10.0 | 8.8 | 8.1 | 9.3 |
| 300%/100% | 5.1 | 4.5 | 4.6 | 4.4 | 4.2 | 4.0 | 4.5 |

TABLE 1-C

| Example No. | 18 | 19 | 20 | 21 | 22 |
|---|---|---|---|---|---|
| Prodex 3 | 7.2 | | | | |
| Hydrolysis Y-15099/TEOS/$H_2O$ (1/1/1.5) | | 7.2 | | | |
| Prodex 5 | | | 7.2 | | |
| Prodex 6 | | | | 7.2 | |
| Prodex 4 | | | | | 7.2 |
| Mooney Viscosity @ 100° C. | | | | | |
| ML1 + 4 | 60 | 58 | 59 | 60 | 61 |
| Mooney Scorch @ 135° C. | | | | | |
| $M_v$ | 30.0 | 24.3 | 28.1 | 28.8 | 31.1 |
| MS1+, $t_3$, minutes | 3.6 | 9.1 | 5.1 | 5.0 | 4.3 |
| MS1+, $t_{18}$, minutes | 5.4 | 12.6 | 7.1 | 7.1 | 5.6 |

TABLE 1-D

| Example No. | 18 | 19 | 20 | 21 | 22 |
|---|---|---|---|---|---|
| ODR @ 149° C., 1° arc, 30 minute timer | | | | | |
| $M_L$ in.-lb. | 7.7 | 6.6 | 7.6 | 7.6 | 8.1 |
| $M_H$, in.-lb. | 25.6 | 26.5 | 25.2 | 25.1 | 24.9 |
| $t_{S1}$, minutes | 3.2 | 5.2 | 3.2 | 3.3 | 2.5 |
| t90, minutes | 8.4 | 13.1 | 8.4 | 10.3 | 9.2 |
| Physical Properties, cured t90 @ 149° C. | | | | | |
| Hardness, Shore A | 55 | 57 | 54 | 55 | 55 |
| Elongation, % | 564 | 660 | 549 | 584 | 518 |
| 25% Modulus, psi | 102 | 116 | 107 | 110 | 108 |
| 100% Modulus, psi | 237 | 239 | 232 | 251 | 247 |
| 300% Modulus, psi | 1,183 | 1,070 | 1,170 | 1,190 | 1,274 |
| Tensile, psi | 3,380 | 3,433 | 3,229 | 3,400 | 3,154 |
| 300%/25% | 11.6 | 9.2 | 10.9 | 10.8 | 11.8 |
| 300%/100% | 5.0 | 4.5 | 5.0 | 4.7 | 5.2 |

In view of the many changes and modifications that can be made without departing from principles underlying the invention, reference should be made to the appended claims for an understanding of the scope of the protection to be afforded the invention.

What is claimed is:

1. A blocked mercaptosilane condensate comprising at least one component whose chemical structure is represented by Formula 1:

$$(W1)_l(W2)_m(W3)_y(W4)_u(W5)_v(W6)_w \qquad \text{Formula 1}$$

wherein:

l and at least one subscript selected from the group consisting of m, y, u, v, and w is an integer from 1 to 10,000;

W1 is a hydrolyzable blocked mercaptosilane fragment derived from a hydrolyzable blocked mercaptosilane by replacement of at least one hydrolyzable group with one end of a siloxane oxygen (—O—) group that is represented by either Formula 2 or Formula 3:

$$\{[(ROC(=O)—)_p(G-)_j]_kY—S—\}_rG(—SiX_3)_s \qquad \text{Formula 2:}$$

$$\{(X_3Si—)_qG\}_a\{Y(—S-G-SiX_3)_b\}_c; \qquad \text{Formula 3:}$$

W2 is a hydrolyzable mercaptosilane fragment derived from a hydrolyzable mercaptosilane by replacement of at least one hydrolyzable group with one end of a siloxane oxygen (—O—) group that is represented by Formula 4:

$$\{[(ROC(=O)—)_p(G-)_j]_kY—S—\}_{r-d}G(—SH)_d(—SiX_3)_s; \qquad \text{Formula 4:}$$

W3 is a hydrolyzable polysulfide silane fragment derived from a polysulfide silane by replacement of at least one hydrolyzable group with one end of a siloxane oxygen (—O—) group that is represented by Formula 5:

$$X^1X^2X^3Si\text{-}G^1\text{-}S_x\text{-}G^1\text{-}SiX^1X^2X^3; \qquad \text{Formula 5:}$$

W4 is a hydrolyzable alkyl silane fragment derived from a hydrolyzable alkyl silane by replacement of at least one hydrolyzable group with one end of a siloxane oxygen (—O—) group that can be represented by Formula 6:

$$Y^1Y^2Y^3Si\text{-}R^2; \qquad \text{Formula 6:}$$

W5 is a hydrolyzable bis silyl alkane fragment derived from a hydrolyzable bis silyl alkane by replacement of at least one hydrolyzable group with one end of a siloxane oxygen (—O—) group that is represented by Formula 7:

$$Z^1Z^2Z^3Si\text{-}J\text{-}SiZ^1Z^2Z^3; \qquad \text{Formula 7:}$$

W6 is a hydrolyzable tris silyl alkane fragment derived from a hydrolyzable tris silyl alkane by replacement of at least one hydrolyzable group with one end of a siloxane oxygen (—O—) group that is represented by either Formula 8 or Formula 9:

$$(Z^1Z^2Z^3Si—CH_2CH_2—)_3C_6H_9 \qquad \text{Formula 8:}$$

$$(Z^1Z^2Z^3Si—CH_2CH_2CH_2—)_3N_3C_3O_3; \qquad \text{Formula 9:}$$

wherein, in the preceding Formulae 2 through 9:

Y is a polyvalent species $(Q)_zA(=E)$;

A is selected from the group consisting of carbon, sulfur, phosphorus, and sulfonyl;

E is selected from the group consisting of oxygen, sulfur, and NR;

each G is independently selected from the group consisting of monovalent and polyvalent moieties derived by substitution of alkyl, alkenyl, aryl, or aralkyl moieties, wherein G comprises from 1 to 18 carbon atoms; provided that G is not such that the silane would contain an, alpha, beta-unsaturated carbonyl including a carbon-carbon double bond next to the thiocarbonyl group, and provided that, if G is univalent, i.e., if p is 0, G can be hydrogen;

in each case, the atom A attached to the unsaturated heteroatom E is attached to the sulfur, which in turn is linked via a group G to the silicon atom;

Q is selected from the group consisting of oxygen, sulfur, and (—NR—);

each R is independently selected from the group consisting of hydrogen; straight, cyclic, or branched alkyl that may or may not contain unsaturation; alkenyl groups; aryl groups; and aralkyl groups, wherein each R, other than where R is hydrogen, comprises from 1 to 18 carbon atoms;

each X is independently selected from the group consisting of —Cl, —Br, RO—, RC(=O)O—, $R_2C=NO$—, $R_2NO$—, $R_2N$—, —R, —$(OSiR_2)_t(OSiR_3)$, and $(-O-)_{0.5}$ wherein each R is as above and at least one X is not —R;

$R^1$, $R^2$, and $R^3$ are independently selected from the group consisting of hydrocarbon fragments obtained by removal of one hydrogen atom from a hydrocarbon having from 1 to 20 carbon atoms including aryl groups and any branched or straight chain alkyl, alkenyl, arenyl, or aralkyl groups;

each J, and $G^1$ are independently selected from the group consisting of hydrocarbon fragments obtained by removal of two hydrogen atom from a hydrocarbon having from 1 to 20 carbon atoms including arylene groups and any branched or straight chain alkylene, alkenylene, arenylene, or aralkylene groups;

each $X^1$ is a hydrolyzable moiety independently selected from the group consisting of —Cl, —Br, —OH, —$OR^1$, $R^1C(=O)O$—, —O—N=$CR^1_2$, and $(-O-)_{0.5}$;

each $X^2$ and $X^3$ is independently selected from the group consisting of hydrogen, the members listed above for $R^1$, and the members listed above for $X^1$;

at least one occurrence of $X^1$, $X^2$, and $X^3$ is $(-O-)_{0.5}$;

$Y^1$ is a moiety selected from hydrolyzable groups consisting of —Cl, —Br, —OH, —OR, $R^2C(=O)O$—, —O—N=$CR^2_2$, and $(-O-)_{0.5}$;

$Y^2$ and $Y^3$ are independently selected from the group consisting of hydrogen, the members listed above for $R^2$, and the members listed above for $Y^1$; and at least one occurrence of $Y^1$, $Y^2$, and $Y^3$ is $(-O-)_{0.5}$;

$Z^1$ is selected from the hydrolyzable groups consisting of —Cl, —Br, —OH, —$OR^3$, $R^3C(=O)O$—, —O—N=$CR^3_2$, and $(-O-)_{0.5}$;

$Z^2$ and $Z^3$ are independently selected from the group consisting of hydrogen, the members listed above for $R^3$, and the members listed above for $Z^1$;

at least one occurrence of $Z^1$, $Z^2$, and $Z^3$ in Formula 7 is $(-O-)_{0.5}$;

$C_6H_9$ in Formula 8 represents any cyclohexane fragment obtainable by removal of three hydrogen atoms from a cyclohexane molecule;

$N_3C_3O_3$ in Formula 9 represents N,N',N''-trisubstituted cyanurate;

a is 0 to 7;
b is 1 to 3;
c is 1 to 6;
d is 1 to r;
j is 0 or 1, but it may be 0 if, and only if, p is 1;
k is 1 to 2;
p is 0 to 5;
q is 0 to 6;
r is 1 to 3;
s is 1 to 3;
t is 0 to 5;
x is 2 to 20;
z is 0 to 2;
provided that:
(a) if A is carbon, sulfur, or sulfonyl, then
  (i) a+b is 2, and
  (ii) k is 1;
(b) if A is phosphorus, then a+b is 3 unless both
  (i) c is greater than 1, and
  (ii) b is 1,
  in which case a is c+1; and
(c) if A is phosphorus, then k is 2.

2. The blocked mercaptosilane condensate of claim 1 wherein l+m+y+u+v+w is equal to at least 2.

3. The blocked mercaptosilane condensate of claim 1 wherein $(Q)_zA(=E)$ is selected from the group consisting of —C(=NR)—; —SC(=NR)—; —SC(=O)—; (—NR)C(=O)—; (—NR)C(=S)—; —OC(=O)—; —OC(=S)—; —C(=O)—; —SC(=S)—; —C(=S)—; —S(=O)—; —S(=O)$_2$—; —OS(=O)$_2$—; (—NR)S(=O)$_2$—; —SS(=O)—; —OS(=O)—; (—NR)S(=O)—; —SS(=O)$_2$—; (—S)$_2$P(=O)—; —(—S)P(=O)—; —P(=O)(—)$_2$; (—S)$_2$P(=S)—; —(—S)P(=S)—; —P(=S)(—)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—.

4. The blocked mercaptosilane condensate of claim 1 wherein the functional groups —YS— present in the hydrolyzable blocked mercaptosilane silane fragments are selected from the group consisting of thiocarboxylate esters, dithiocarboxylate, -thiocarbonate esters, dithiocarbonate esters, trithiocarbonate esters, thiocarbamate esters, dithiocarbamate esters,; thiosulfonate esters, thiosulfate esters, thiosulfamate esters, thiosulfinate esters, thiosulfite esters, thiosulfimate esters, thiophosphate esters, dithiophosphate esters, trithiophosphate esters, tetrathiophosphate esters P(=S)(S—)$_3$; thiophosphamate esters, dithiophosphamate esters, thiophosphorammidate esters, (dithiophosphoramidate esters, and trithiophosphoramidate esters.

5. The blocked mercaptosilane condensate of claim 1 wherein the Y groups are selected from the group consisting of —C(=NR)—; —SC(=NR)—; —SC(=O)—; —OC(=O)—; —S(=O)—; —S(=O)$_2$—; —OS(=O)$_2$—; —(NR)S(=O)$_2$—; —SS(=O)—; —OS(=O)—; —(NR)S(=O)—; —SS(=O)$_2$—; (—S)$_2$P(=O)—; —(—S)P(=O)—; —P(=O)(—)$_2$; (—S)$_2$P(=S)—; —(—S)P(=S)—; —P(=S)(—)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—;

(—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—.

6. The blocked mercaptosilane condensate of claim 5 wherein the Y groups are selected from the group consisting of —OC(=O)—; —SC(=O)—; —S(=O)—; —OS(=O)—; —(—S)P(=O)—; and —P(=O)(—)$_2$.

7. The blocked mercaptosilane condensate of claim 1 wherein Y is RC(=O)— in which R has a primary carbon attached to the carbonyl and is a C$_2$-C$_{12}$ alkyl.

8. The blocked mercaptosilane condensate of claim 1 wherein the chemical structure is X$_3$SiGSC(=O)GC(=O)SGSiX$_3$ wherein G is a divalent hydrocarbon.

9. The blocked mercaptosilane condensate of claim 1 wherein G is selected from the group consisting of —(CH$_2$)$_n$— wherein n is 1 to 12, diethylene cyclohexane, 1,2,4-triethylene cyclohexane, and diethylene benzene and the sum of the carbon atoms within the G groups within the molecule is from 3 to 18.

10. The blocked mercaptosilane condensate of claim 1 wherein each R group is independently selected from the group consisting of hydrogen, C$_6$ to C$_{10}$ aryl, and C$_1$ to C$_6$ alkyl.

11. The blocked mercaptosilane condensate of claim 1 wherein each X is independently selected from the group consisting of methoxy, ethoxy, propoxy, isopropoxy, isobutoxy, acetoxy, and oximato, provided that at least one X is hydrolyzable and at least one occurrence of X is (—O—)$_{0.5}$.

12. The blocked mercaptosilane condensate of claim 1 wherein p is 0 to 2; X is RO— or RC(=O)O—; R is hydrogen, phenyl, isopropyl, cyclohexyl, or isobutyl; and G is a substituted phenyl or a substituted straight chain C$_2$ to C$_{12}$ alkyl.

13. The blocked mercaptosilane condensate of claim 12 wherein p is zero, X is ethoxy, and G is a C$_3$-C$_{12}$ alkyl derivative.

14. The blocked mercaptosilane condensate of claim 1 wherein the hydrolyzable blocked mercaptosilane silane fragments are those whose parent silanes are selected from the group consisting of 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5-triethoxysilylpentyl)benzoic acid; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctoate; 3-triethoxysilyl-1-propyl thiopalmitate; 3-triethoxysilyl-1-propyl thiooctoate; 3-triethoxysilyl-1-propyl thiobenzoate; 3-triethoxysilyl-1-propyl thio-2-ethylhexanoate; 3-methyldiacetoxysilyl-1-propyl thioacetate; 3-triacetoxysilyl-1-propyl thioacetate; 2-methyldiacetoxysilyl-1-ethyl thioacetate; 2-triacetoxysilyl-1-ethyl thioacetate; 1-methyldiacetoxysilyl-1-ethyl thioacetate; 1-triacetoxysilyl-1-ethyl thioacetate; tris-(3-triethoxysilyl-1-propyl)trithiophosphate; bis-(3-triethoxysilyl-1-propyl)methyldithiophosphonate; bis-(3-triethoxysilyl-1-propyl)ethyldithiophosphonate; 3-triethoxysilyl-1-propyldimethylthiophosphonate; 3-triethoxysilyl-1-propyldiethylthiophosphinate; tris-(3-triethoxysilyl-1-propyl)tetrathiophosphate; bis-(3-triethoxysilyl-1-propyl)methyltrithiophosphonate; bis-(3-triethoxysilyl-1-propyl)ethyltrithiophosphonate; 3-triethoxysilyl-1-propyldimethyldithiophosphinate; 3-triethoxysilyl-1-propyldiethyldithiophosphinate; tris-(3-methyldimethoxysilyl-1-propyl)trithiophosphate; bis-(3-methyldimethoxysilyl-1-propyl)methyldithiophosphonate; bis-(3-methyldimethoxysilyl-1-propyl)ethyldithiophosphonate; 3-methyldimethoxysilyl-1-propyldimethylthiophosphinate; 3-methyldimethoxysilyl-1-propyldiethylthiophosphinate; 3-triethoxysilyl-1-propylmethylthiosulphate; 3-triethoxysilyl-1-propylmethanethiosulphonate; 3-triethoxysilyl-1-propylethanethiosulphonate; 3-triethoxysilyl-1-propylbenzenethiosulphonate; 3-triethoxysilyl-1-propyltoluenethiosulphonate; 3-triethoxysilyl-1-propylnaphthalenethiosulphonate; 3-triethoxysilyl-1-propylxylenethiosulphonate; triethoxysilylmethylmethylthiosulphate; triethoxysilylmethylmethanethiosulphonate; triethoxysilylmethylethanethiosulphonate; triethoxysilylmethylbenzenethiosulphonate; triethoxysilylmethyltoluenethiosulphonate; triethoxysilylmethylnaphthalenethiosulphonate; and triethoxysilylmethylxylenethiosulphonate.

15. The blocked mercaptosilane condensate of claim 1 wherein X$^1$, Y$^1$, and Z$^1$ are independently selected from the group consisting of methoxy, ethoxy, propoxy, isopropoxy, butoxy, phenoxy, benzyloxy, hydroxy, chloro, and acetoxy.

16. The blocked mercaptosilane condensate of claim 1 wherein X$^2$, X$^3$, Y$^2$, Y$^3$, Z$^2$, and Z$^3$ are independently selected from the group consisting of methoxy, ethoxy, propoxy, isopropoxy, butoxy, phenoxy, benzyloxy, hydroxy, chloro, acetoxy, hydrogen, methyl, ethyl, propyl, isopropyl, sec-butyl, phenyl, vinyl, cyclohexyl, and C$_4$-C$_{20}$, straight-chain alkyl groups.

17. The blocked mercaptosilane condensate of claim 1 wherein X$^1$, X$^2$, and X$^3$ are the same alkoxy group; Y$^1$, Y$^2$, and Y$^3$ are the same alkoxy group; and Z$^1$, Z$^2$, and Z$^3$ are the same alkoxy group.

18. The blocked mercaptosilane condensate of claim 1 wherein R$^2$ is selected from the group consisting of methyl, vinyl, ethyl, propyl, allyl, butyl, methallyl, pentyl, hexyl, phenyl, tolyl, benzyl, octyl, xylyl, mesityl, decyl, dodecyl, hexadecyl, and octadecyl.

* * * * *